US009217681B2

(12) United States Patent
Alemohammad et al.

(10) Patent No.: US 9,217,681 B2
(45) Date of Patent: Dec. 22, 2015

(54) OPTICAL FIBER SENSOR AND METHODS OF MANUFACTURE

(76) Inventors: Hamidreza Alemohammad, Waterloo (CA); Ehsan Toyserkani, Waterloo (CA)

( * ) Notice: Subject to any disclaimer, the term of this patent is extended or adjusted under 35 U.S.C. 154(b) by 335 days.

(21) Appl. No.: 13/384,275

(22) PCT Filed: Jul. 16, 2010

(86) PCT No.: PCT/CA2010/001117
§ 371 (c)(1),
(2), (4) Date: Mar. 30, 2012

(87) PCT Pub. No.: WO2011/006260
PCT Pub. Date: Jan. 20, 2011

(65) Prior Publication Data
US 2012/0177319 A1    Jul. 12, 2012

Related U.S. Application Data

(60) Provisional application No. 61/213,796, filed on Jul. 16, 2009.

(51) Int. Cl.
*G01D 5/353*    (2006.01)
*G02B 6/02*    (2006.01)
(Continued)

(52) U.S. Cl.
CPC ............ *G01L 1/246* (2013.01); *C03C 25/106* (2013.01); *C03C 25/108* (2013.01); *C03C 25/6233* (2013.01); *G01B 11/18* (2013.01); *G01D 5/35303* (2013.01); *G01K 11/3206* (2013.01);
(Continued)

(58) Field of Classification Search
None
See application file for complete search history.

(56) References Cited

U.S. PATENT DOCUMENTS 5,844,667 A    12/1998    Maron
6,044,189 A    3/2000    Miller
(Continued)

FOREIGN PATENT DOCUMENTS

GB    2371360 B    2/2005

OTHER PUBLICATIONS

International Searching Authority/Canadian Intellectual Patent Office, International Preliminary Report on Patentability (Form PCT/IB/373) for International Patent Appln No. PCT/CA2010/001117 dated Jan. 17, 2012, Quebec Canada.
(Continued)

*Primary Examiner* — Jerry Rahll
(74) *Attorney, Agent, or Firm* — Gowling Lafleur Henderson LLP; Neil Henderson

(57) ABSTRACT

A superstructure fiber Bragg gratings (FBG) by laser-assisted direct writing of on-fiber metallic films. A laser direct write method is used to fabricate periodic films of silver nanoparticles on the non-planar surface of as-fabricated FBGs. Silver films with a thickness of about 9 μm are fabricated around a Bragg grating optical fiber. The performance of the superstructure FBG is studied by applying temperature and tensile stress on the fiber. An opto-mechanical model is also developed to predict the optical response of the synthesized superstructure FBG under thermal and structural loadings. The reflectivity of sidebands in the reflection spectrum can be tuned up to 20% and 37% under thermal and structural loadings, respectively. In addition, the developed superstructure FBG is used for simultaneous measurement of multiple criteria such as force and temperature to eliminate the inherent limitation of regular FBGs in multi-parameter sensing.

24 Claims, 31 Drawing Sheets

Periodic films on FBG and their effects on the average index of refraction ($\overline{Dn}$) when the optical fiber is exposed to axial tensile force and/or temperature variations

(51) Int. Cl.
*G01L 1/24* (2006.01)
*C03C 25/10* (2006.01)
*C03C 25/62* (2006.01)
*G01B 11/16* (2006.01)
*G01K 11/32* (2006.01)
*G01N 21/77* (2006.01)

(52) U.S. Cl.
CPC .......... *G01N 21/774* (2013.01); *G02B 6/02204* (2013.01)

(56) References Cited

U.S. PATENT DOCUMENTS

| | | | |
|---|---|---|---|
| 6,187,700 B1 | 2/2001 | Merkel | |
| 6,233,746 B1 | 5/2001 | Skinner | |
| 6,303,182 B1 | 10/2001 | Eggleton et al. | |
| 6,349,165 B1 | 2/2002 | Lock | |
| 6,351,585 B1 | 2/2002 | Amundson et al. | |
| 6,377,727 B1 | 4/2002 | Dariotis et al. | |
| 6,427,040 B1 | 7/2002 | Ahuja et al. | |
| 6,876,785 B1 | 4/2005 | Li et al. | |
| 6,923,048 B2 | 8/2005 | Willsch et al. | |
| 7,116,846 B2 | 10/2006 | Methe et al. | |
| 7,228,017 B2 | 6/2007 | Xia et al. | |
| 7,272,285 B2 | 9/2007 | Benoit et al. | |
| 7,539,361 B2 | 5/2009 | Dimmick et al. | |
| 2002/0041723 A1 | 4/2002 | Ronnekleiv et al. | |
| 2002/0141699 A1 | 10/2002 | Lo et al. | |
| 2004/0184700 A1 | 9/2004 | Li et al. | |
| 2006/0115195 A1 | 6/2006 | Kobayashi et al. | |
| 2009/0087303 A1 | 4/2009 | Ruggiero et al. | |

OTHER PUBLICATIONS

Smart Fibres Ltd., "Overview and Capability Statement for Permanent Downhole Monitoring of Multi-Point Pressure and Temperature with Fibre Bragg Grating Sensing Technology", www.smartfibres.com, Bracknell, United Kingdom.
Hamidreza Alemohammad and Ehsan Toyserkani, "Simultaneous Measurement of Temperature and Tensile Loading Using Superstructure FBGs Developed by Laser Direct Writing of Periodic On-Fiber Metallic Films", Smart Materials and Structures IOP Publishing Ltd, pp. 1-10, Aug. 20, 2009, UK.
State Intellectual Property Office of China, Office Action on Chinese Patent Appln. No. 201080031882.8, dated Nov. 14, 2014.
State Intellectual Property Office of China, Office Action on Chinese Patent Appln. No. 201080031882.8, dated Apr. 27, 2015.

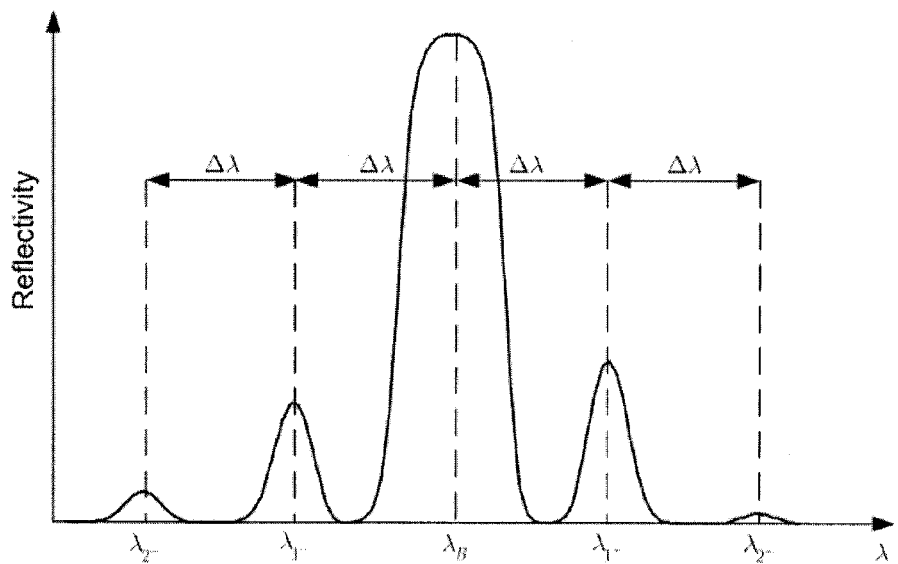
Figure 1: Reflection spectrum of superstructure FBG with the equally spaced side bands
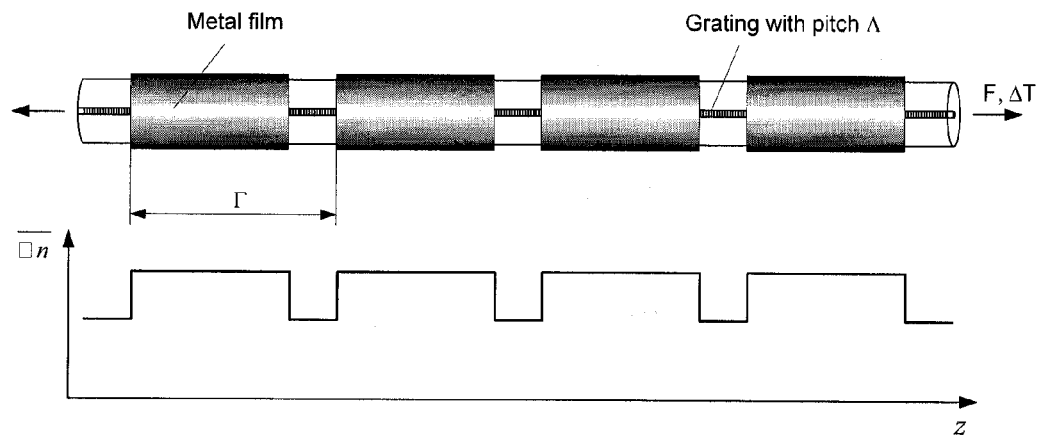
Figure 2: Periodic films on FBG and their effects on the average index of refraction ($\overline{Dn}$) when the optical fiber is exposed to axial tensile force and/or temperature variations

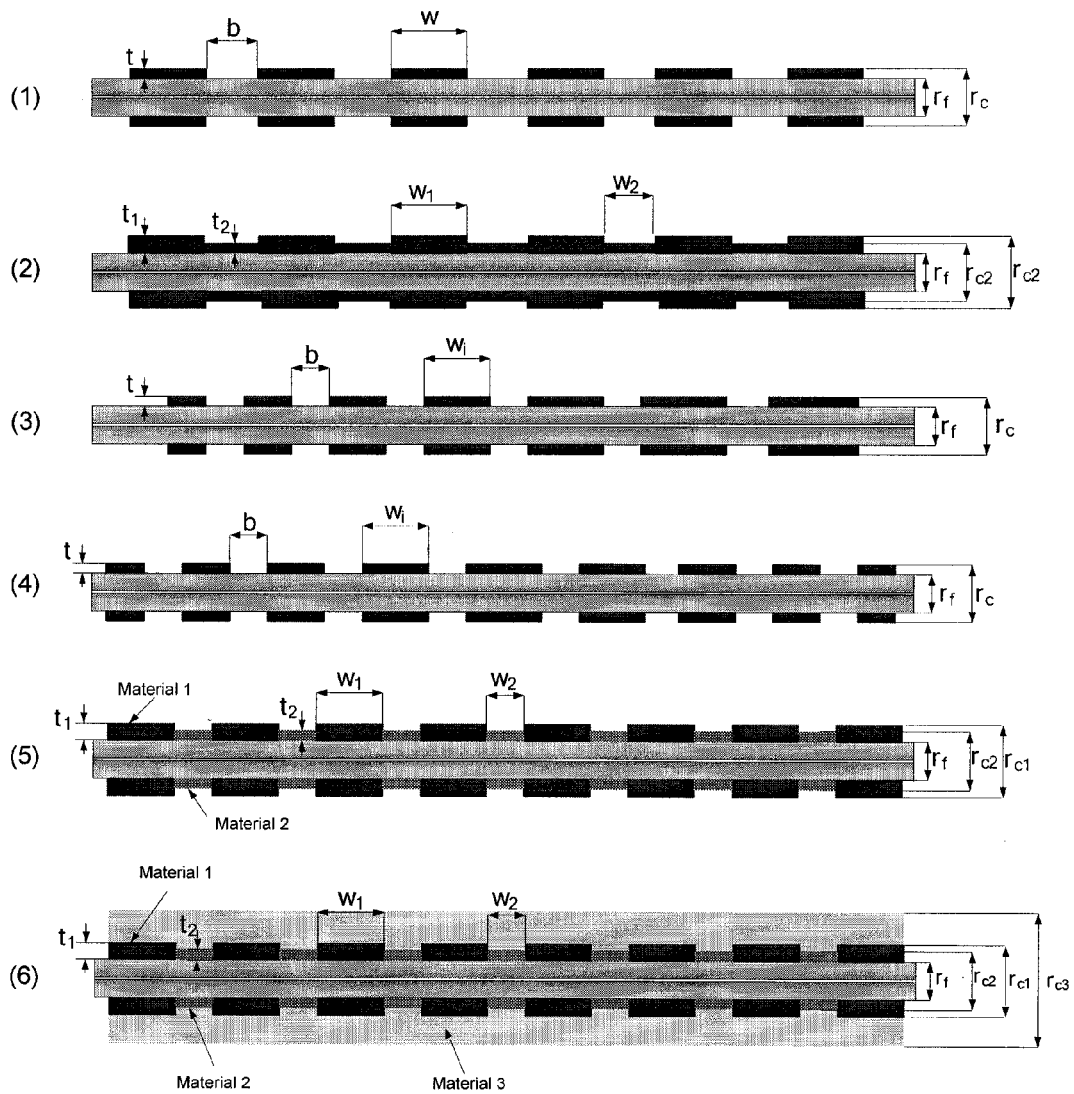
Figure 3: Different patterns of coatings for making superstructure FBGs for simultaneous measurement of strain and temperature

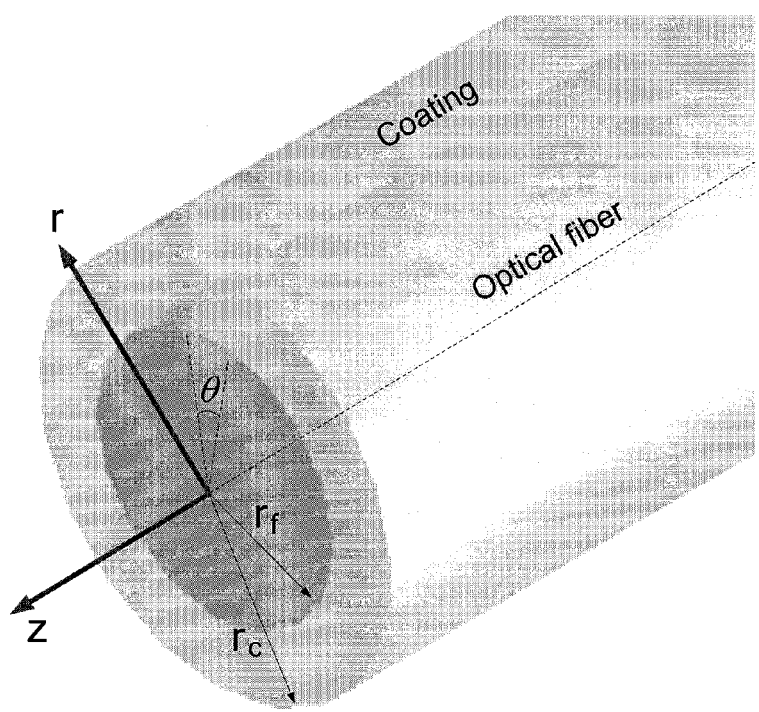
Figure 4: Coated segment of an optical fiber in cylindrical coordinates

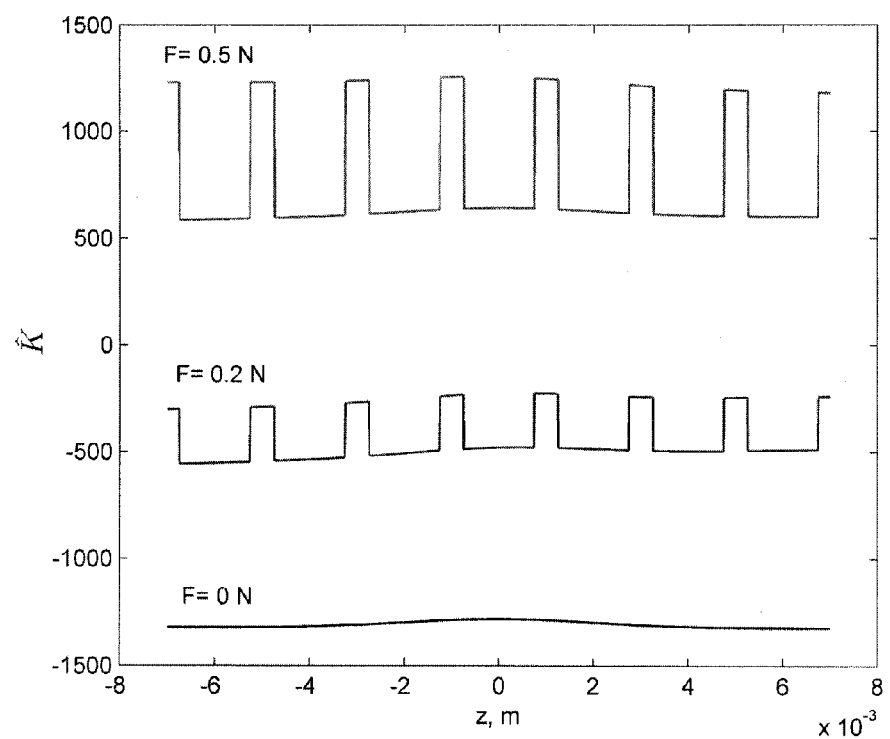
Figure 5 : $\hat{K}$ at the wavelength of 1550 nm along SFBG with a grating length of 14 mm at different tensile forces and $\Delta T = 0$

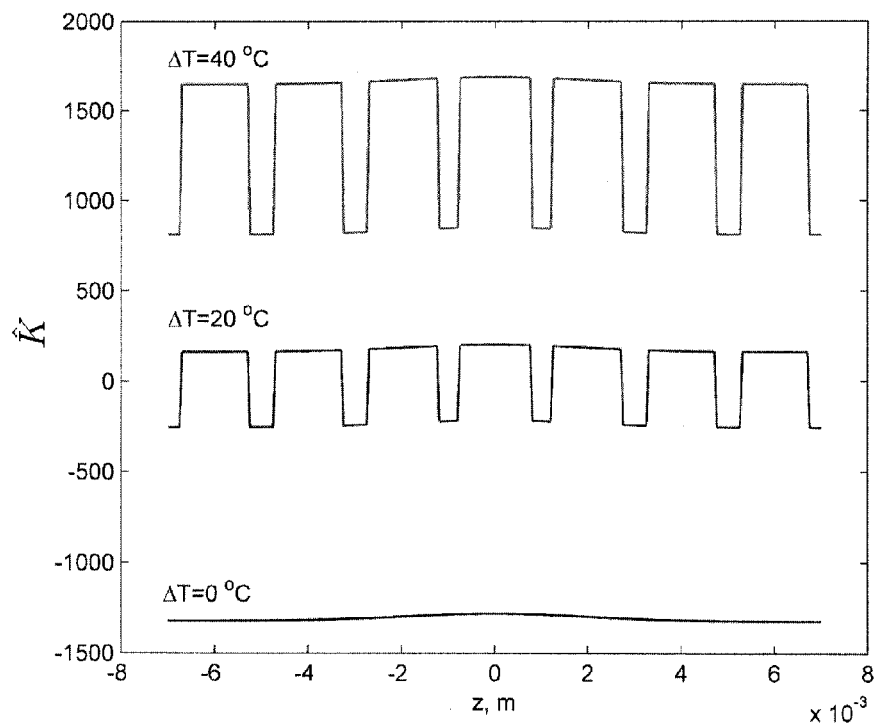
Figure 6: $\hat{K}$ at the wavelength of 1550 nm along SFBG with the grating length of 14 mm at different temperatures and F = 0
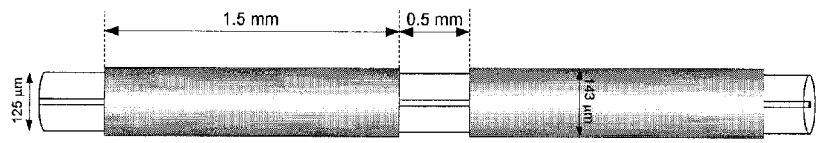
Figure 7: Geometrical dimensions of periodic silver films deposited on FBG

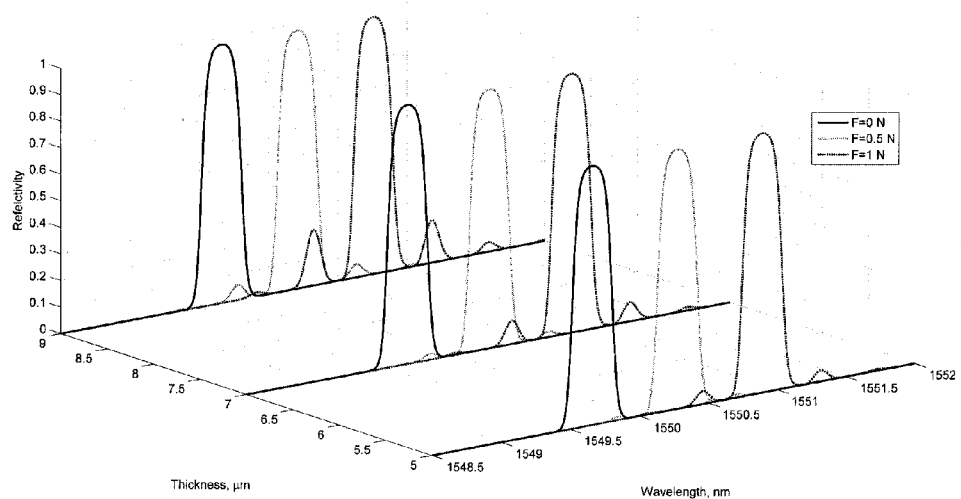
Figure 8: Reflection spectra as a function of applied tensile force for SFBG with silver film thicknesses of 5 μm, 7 μm, and 9 μm

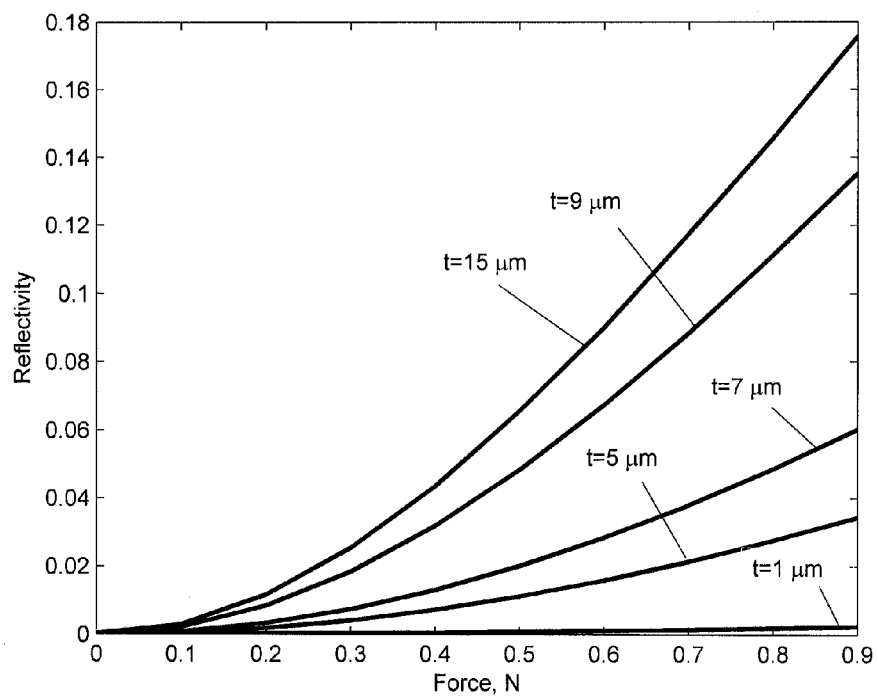
Figure 9: Reflectivity of the first upper sideband as a function of applied tensile force on SFBG with different film thicknesses

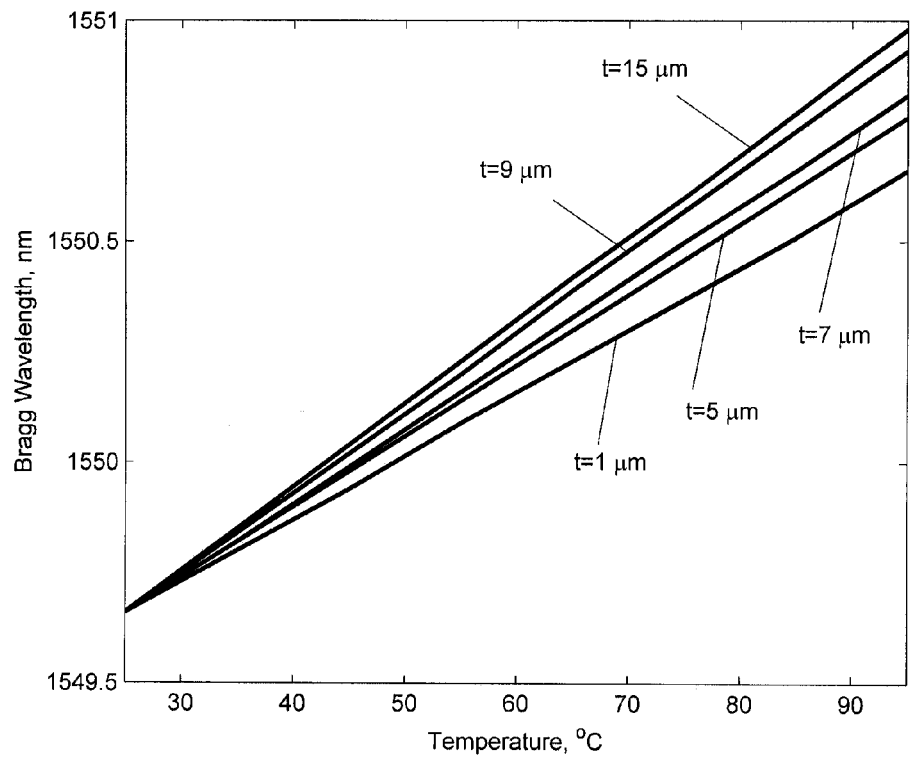
Figure 13: Bragg wavelength shift as a function of temperature for SFBG with different film thicknesses
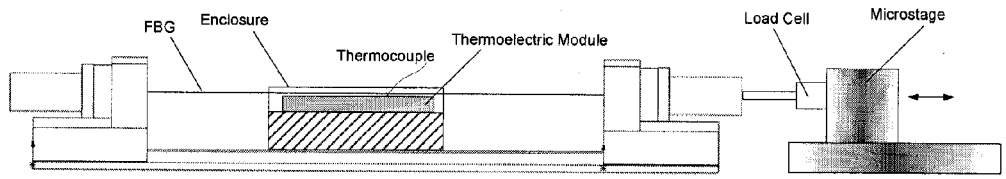
Figure 14: Test setup for axial loading of SFBG at different temperatures

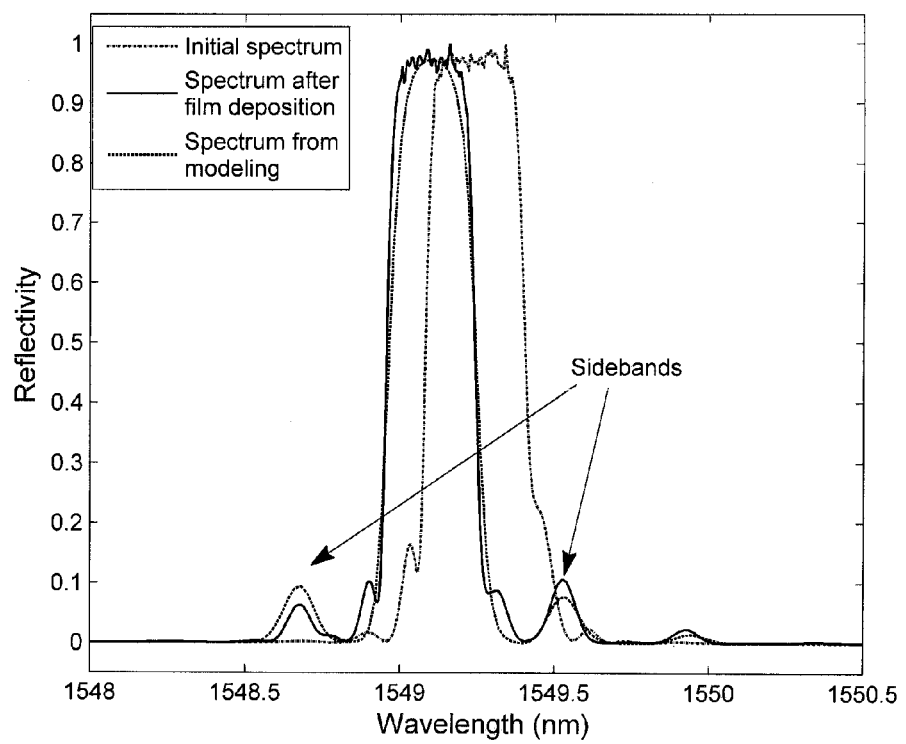
Figure 15: Reflection spectra of FBG before and after the deposition of the on-fiber silver films showing the effects of residual stress

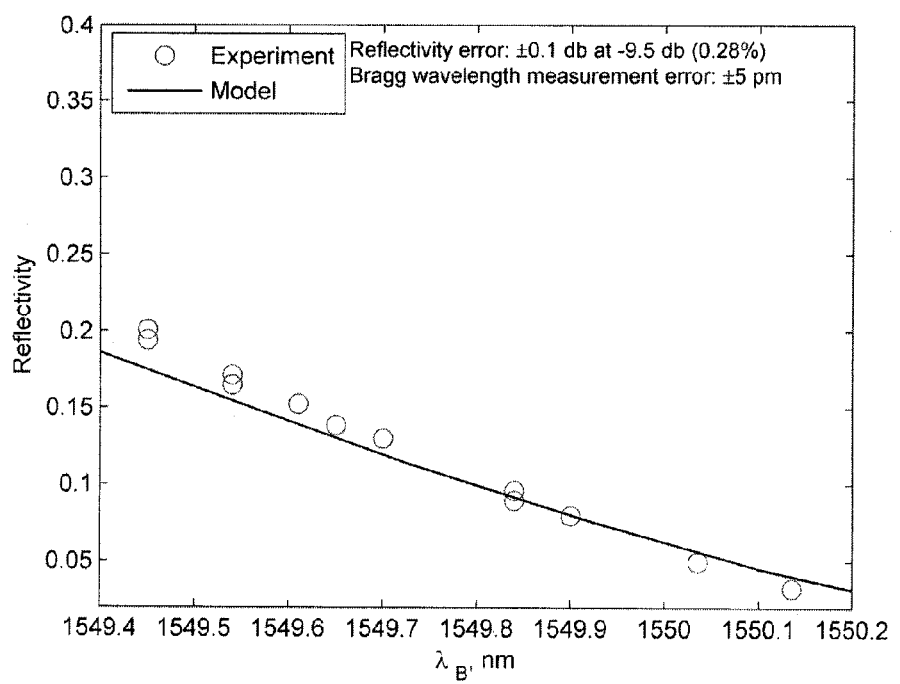
Figure 16: Reflectivity of the first upper sideband as a function of the Bragg wavelength in a thermal cycle

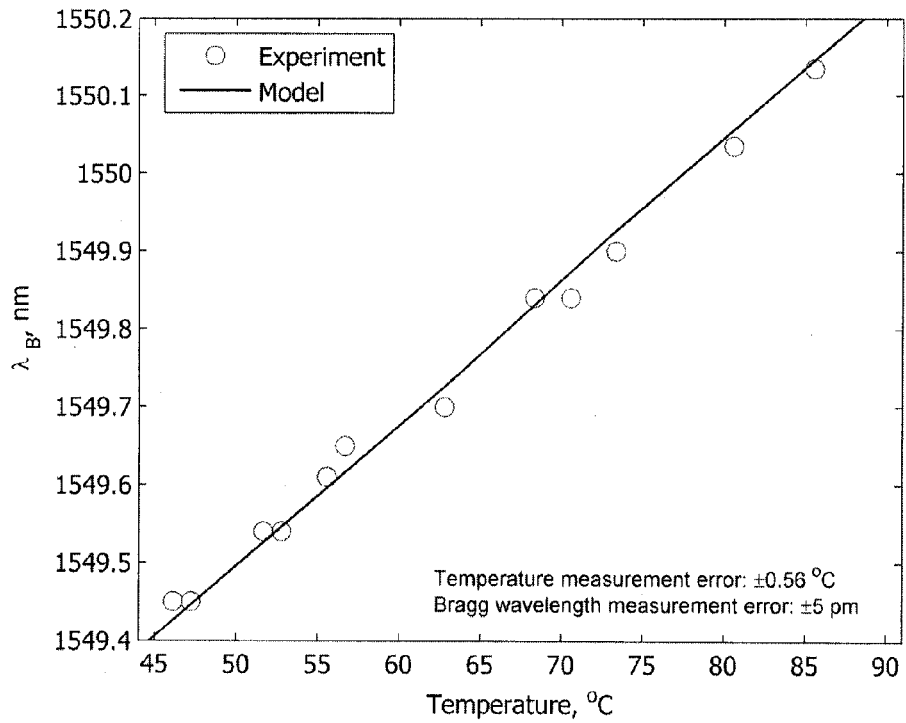
Figure 17: Bragg wavelength as a function of temperature
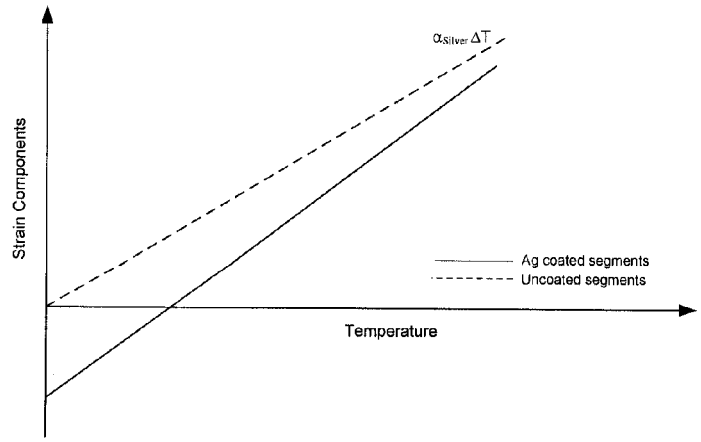
Figure 18: Strain components in the coated and uncoated segments of the optical fiber and between the films and the optical fiber.

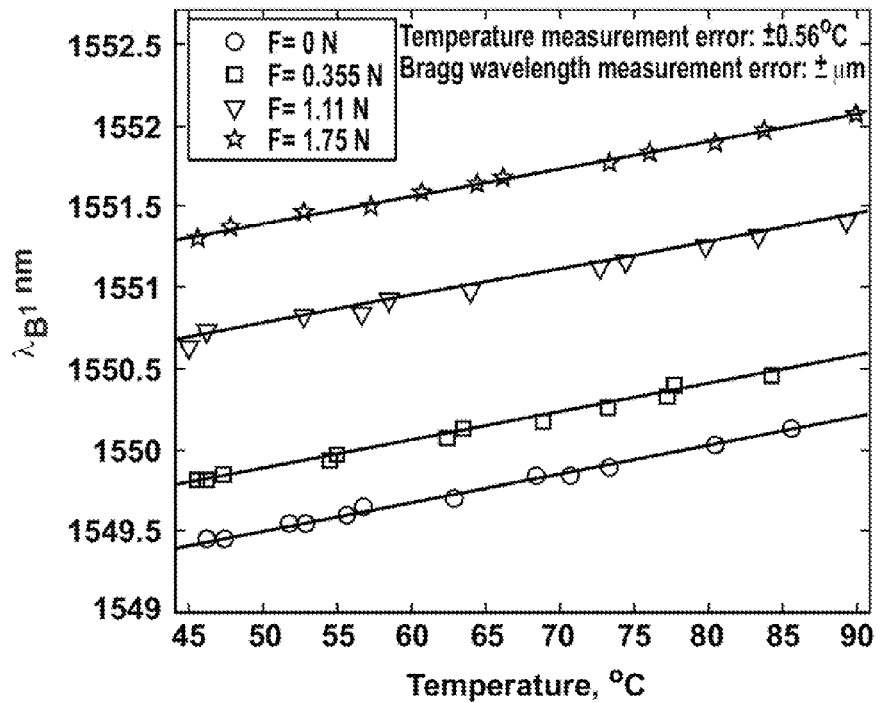
FIG. 23
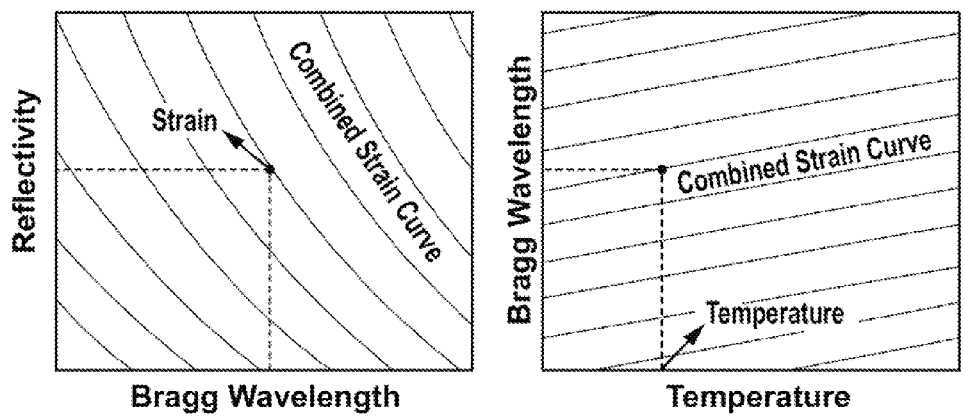
FIG. 24a  FIG. 24b

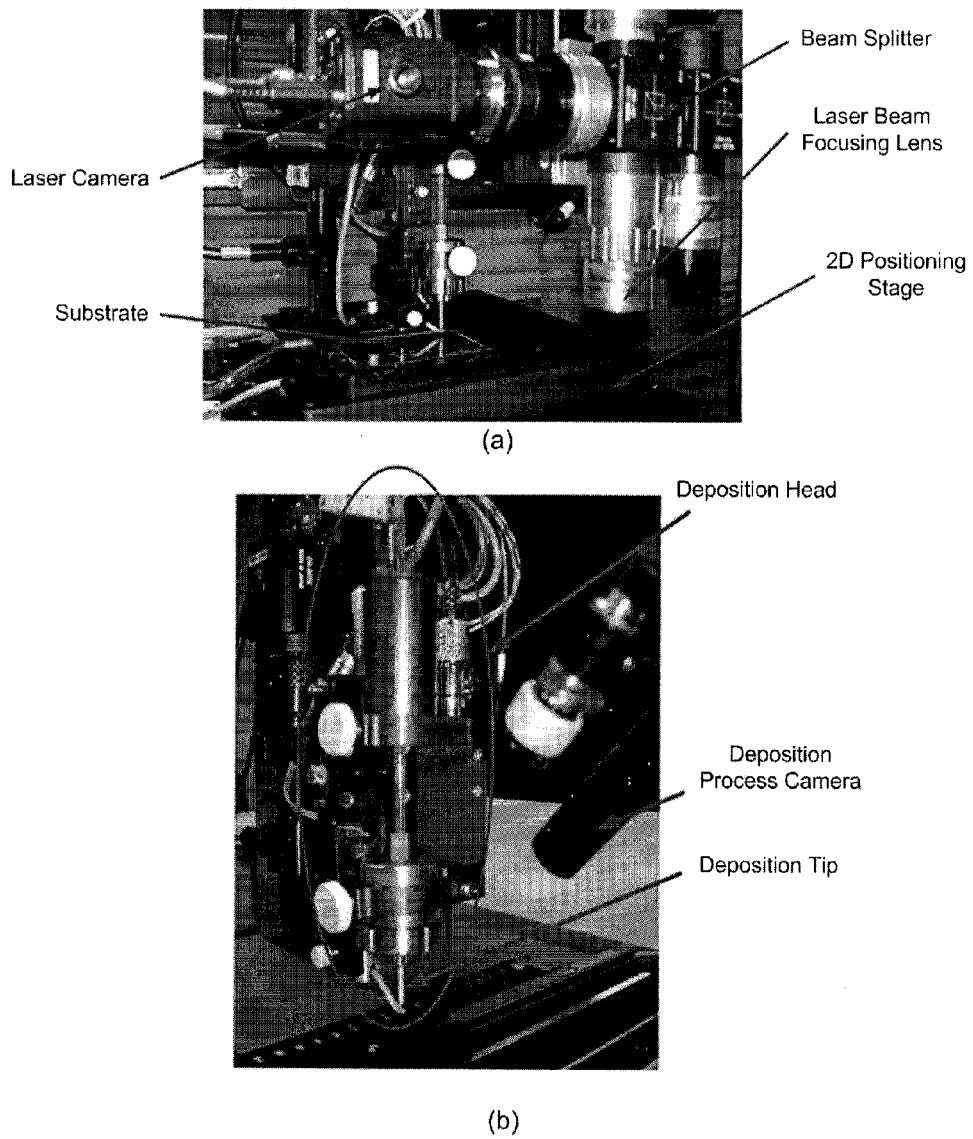
Figures 25a and 25b: LAMM workstation setup (a) laser processing and deposition heads and (b) deposition head

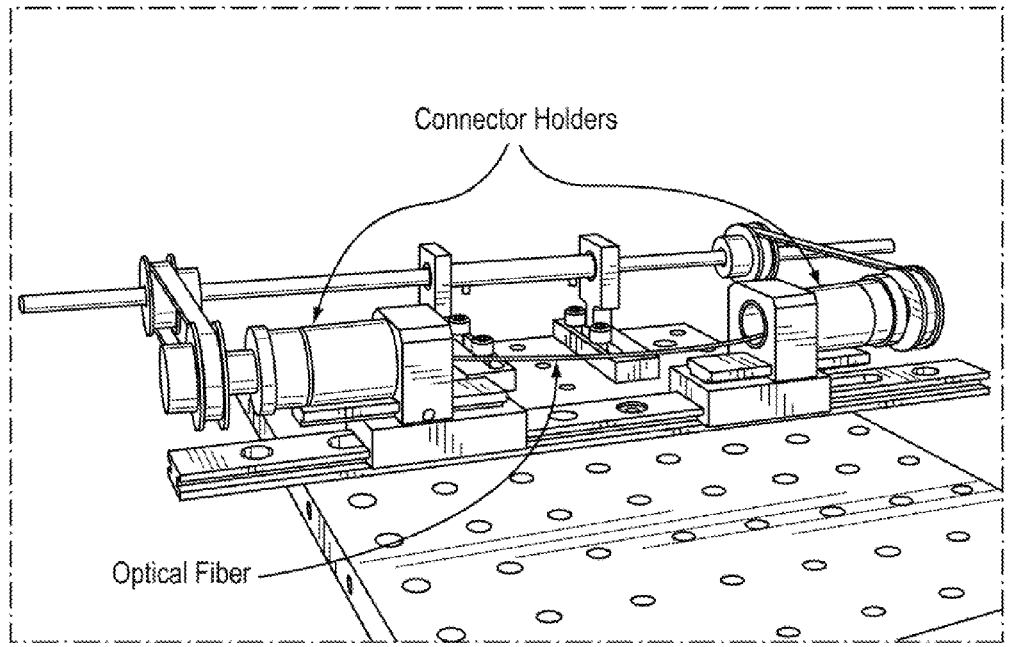
FIG. 26 Rotational stage for the installation of optical fibers in the LAMM workstation
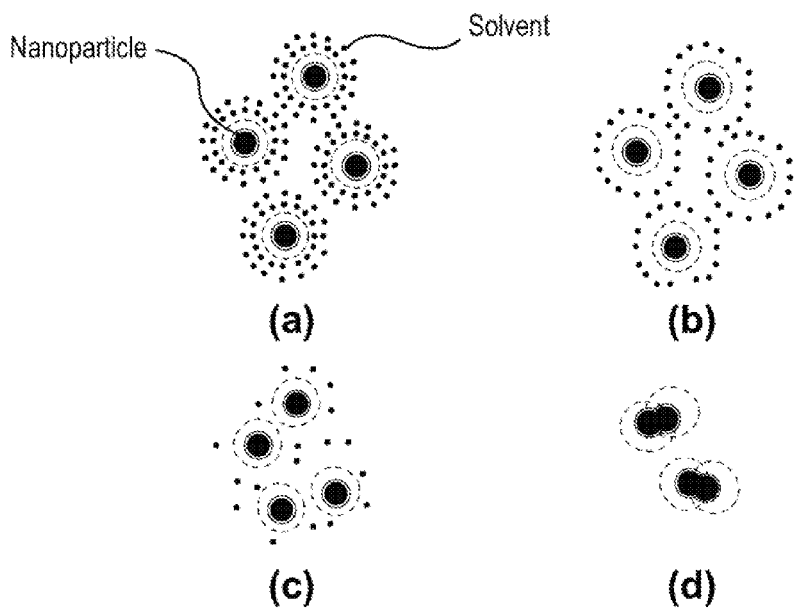
FIG. 27 Laser sintering mechanism of nanoparticles (a) before sintering, (b) liquidevaporation, (c) start of abblomeration, and (d) end of agglomeration

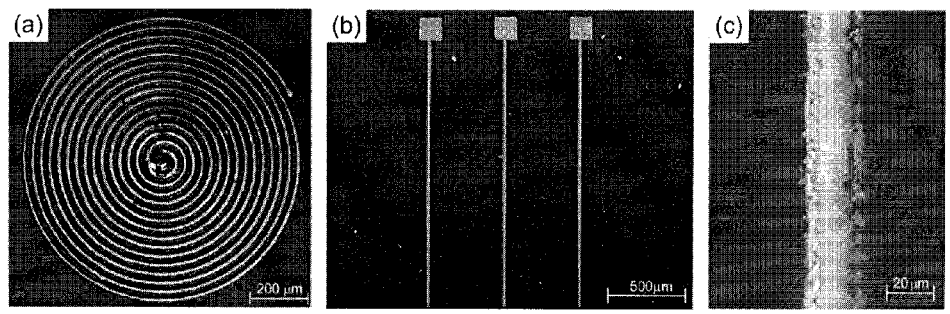

Figures 28 a to c: Typical deposition patterns on a planar silica substrate, (a) spiral pattern, (b) conductive lines
with pads at the ends, and (c) magnified images of the conductive lines in (b).
Atomizer gas flow rate: 12 cm$^3$/min, sheath gas flow rate: 50 cm$^3$/min, deposition velocity: 0.5 mm/s, laser power: 0.8 W, laser scanning speed: 0.25 mm/s for the lines and 1 mm/s for the spiral pattern

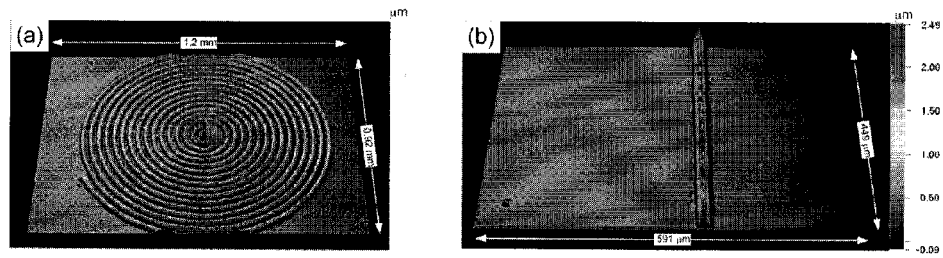

Figures 29a and b: Topography images of the deposition patterns in Figure 4-5 taken by optical profiling
system (a) spiral pattern and (b) lines

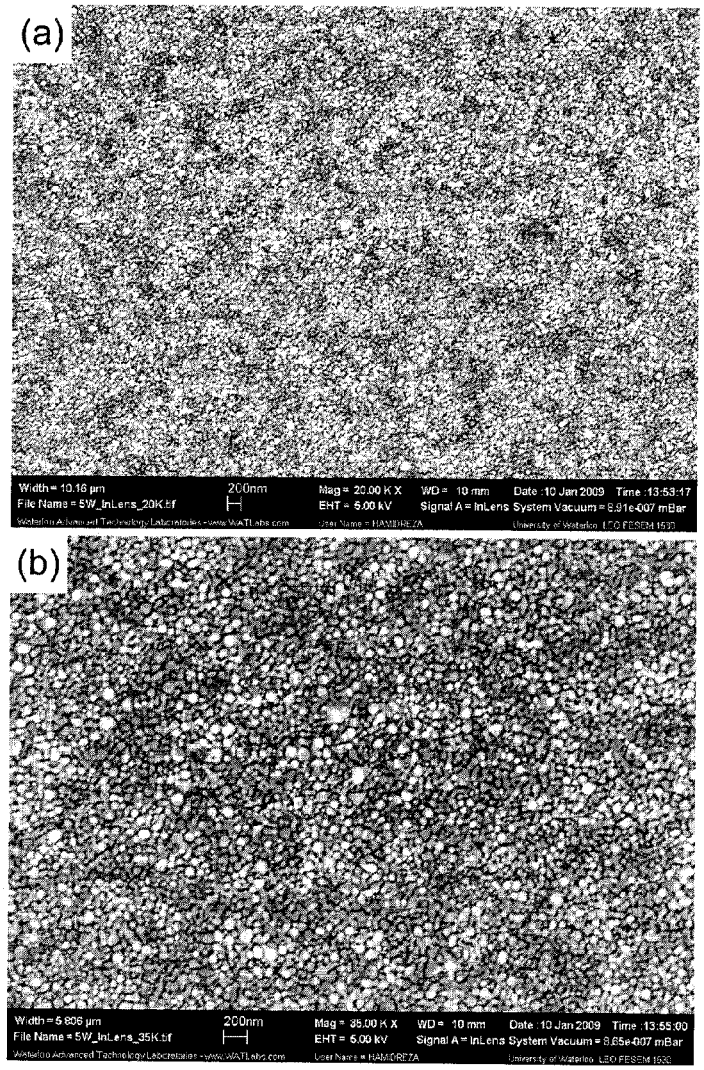
Figures 30 a and b: In-lens images of the microstructure of the silver thin films sintered at 1.35 W taken at magnifications of (a) 20 kX and (b) 35 kX

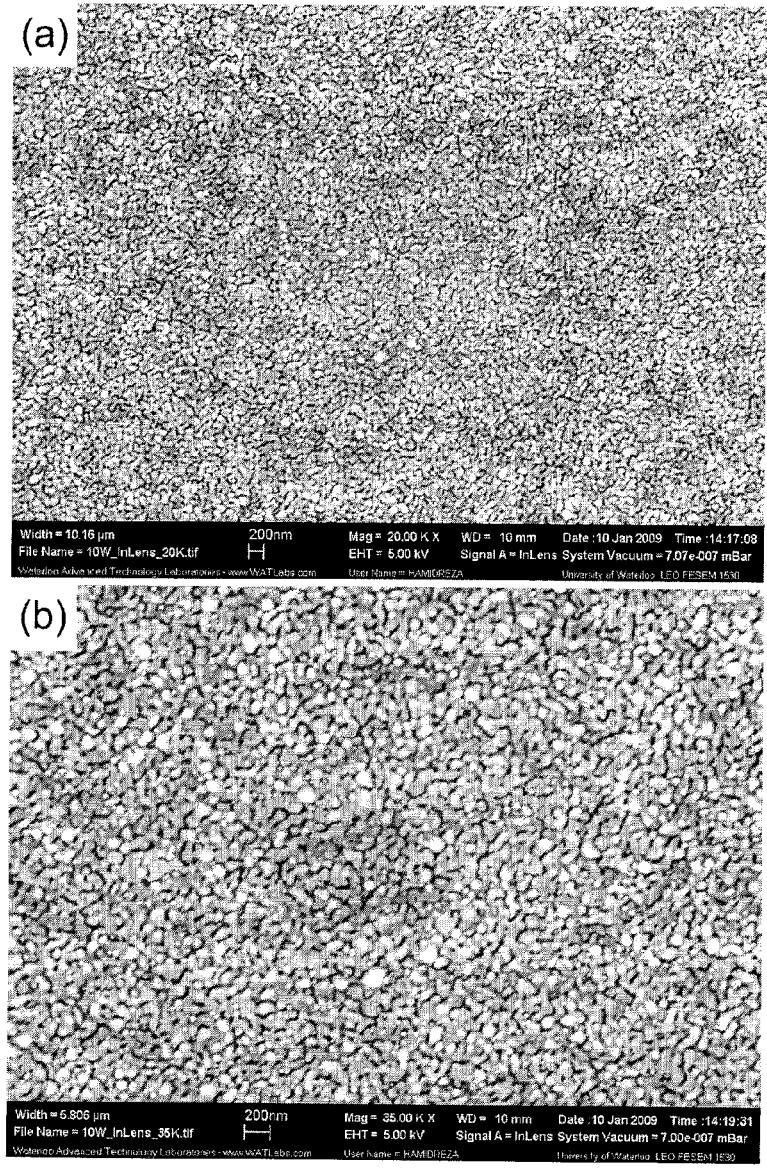
Figures 31 a and b: In-lens images of the microstructure of the silver thin films sintered at 3.28 W at magnifications of (a) 20 kX and (b) 35 kX

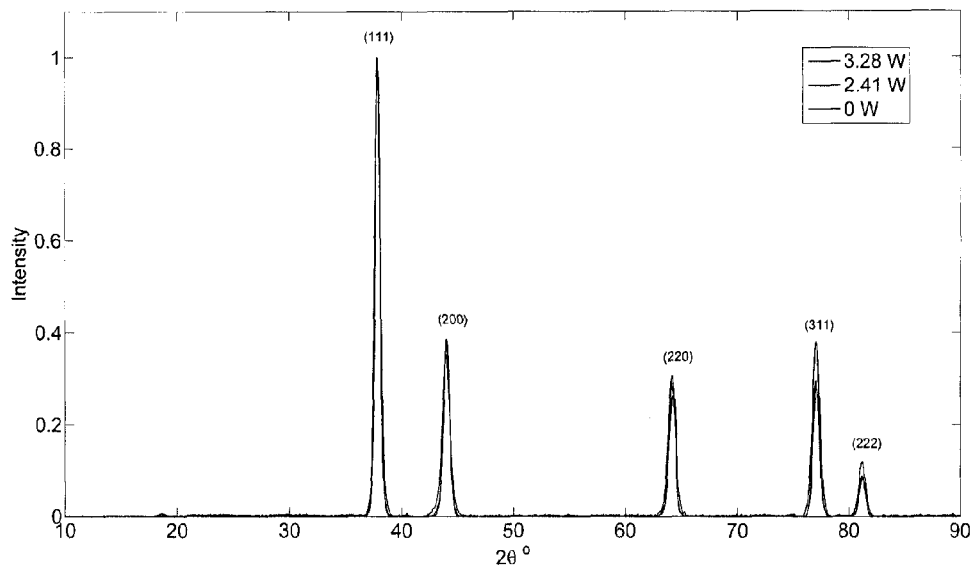
Figure 32: XRD spectra of the silver thin films sintered at different laser powers
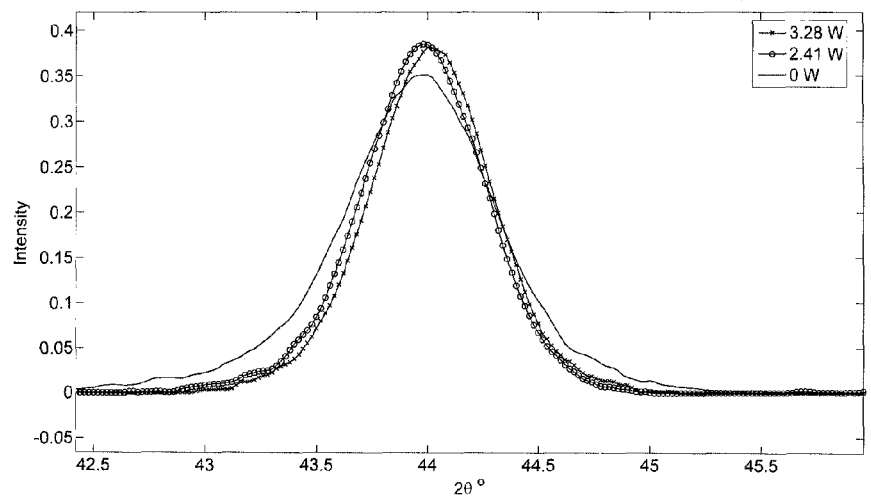
Figure 33: XRD peaks for (200) planes at different laser powers

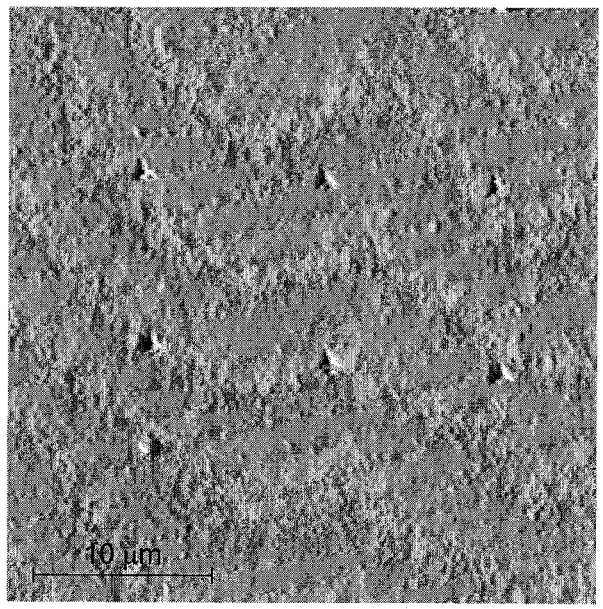
Figure 34: Nanoindentation profiles at six locations on a silver thin film

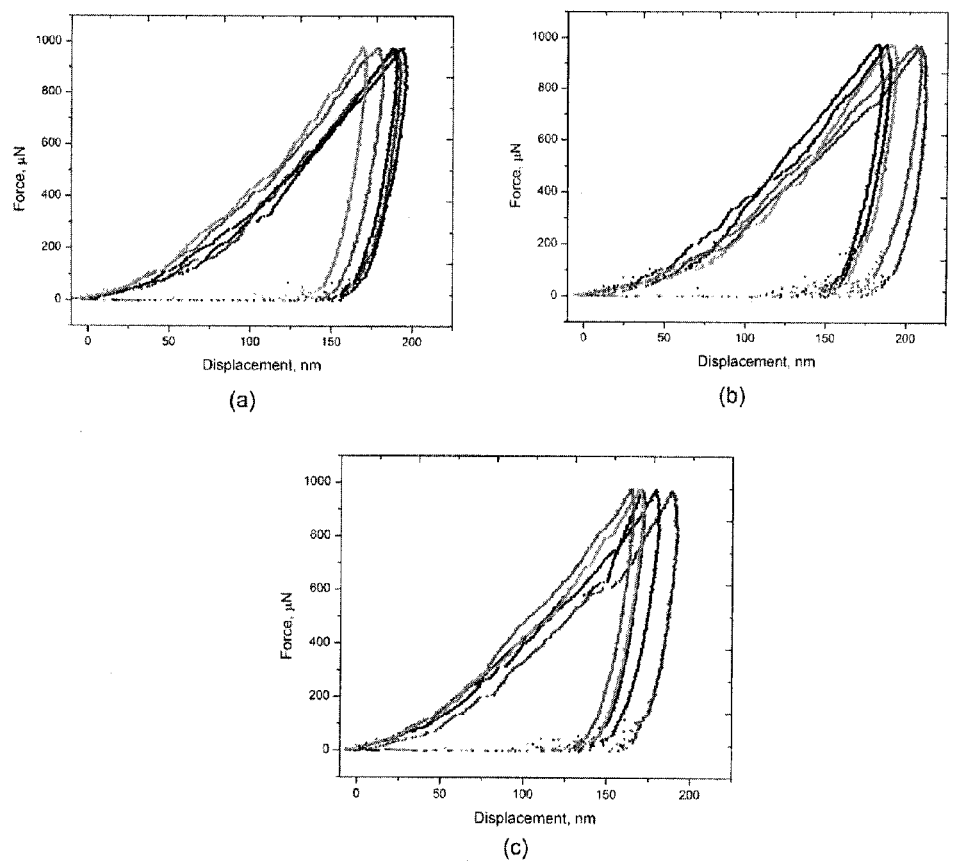
Figures 35 a to c: Load displacement curves obtained from the nanoindentation test at five locations of the silver thin films sintered at (a) 1.35 W, (b) 2.41 W, and (c) 3.28 W

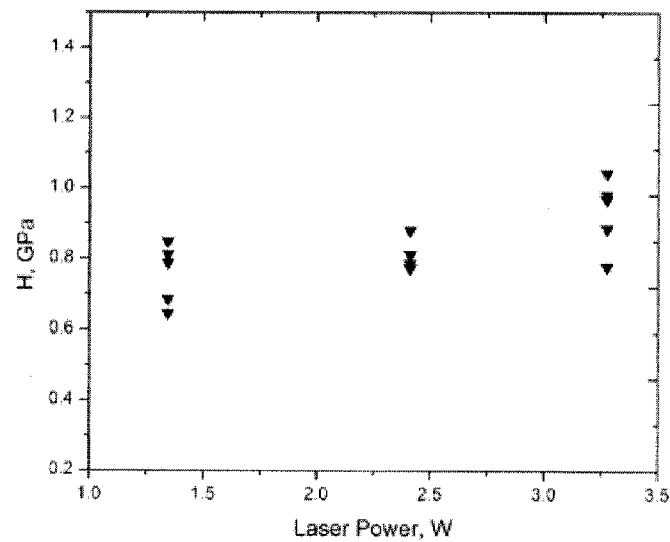
Figure 36: Hardness of silver thin films as a function of incident laser power obtained from nanoindentation tests
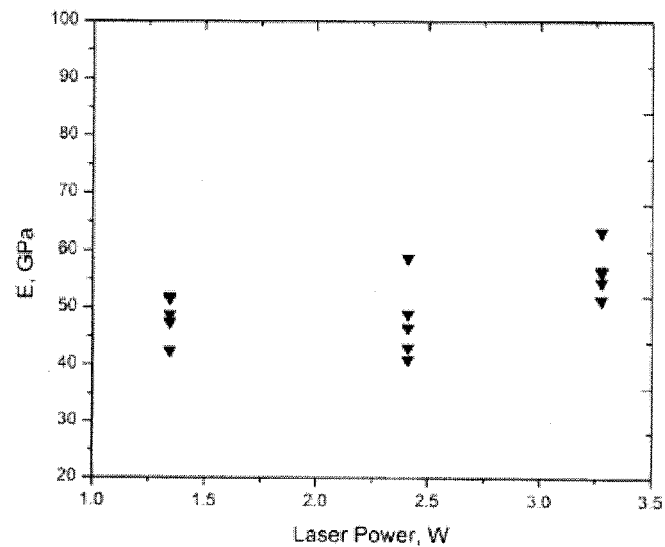
Figure 37: Modulus of elasticity of silver thin films as a function of incident laser power obtained from nanoindentation tests

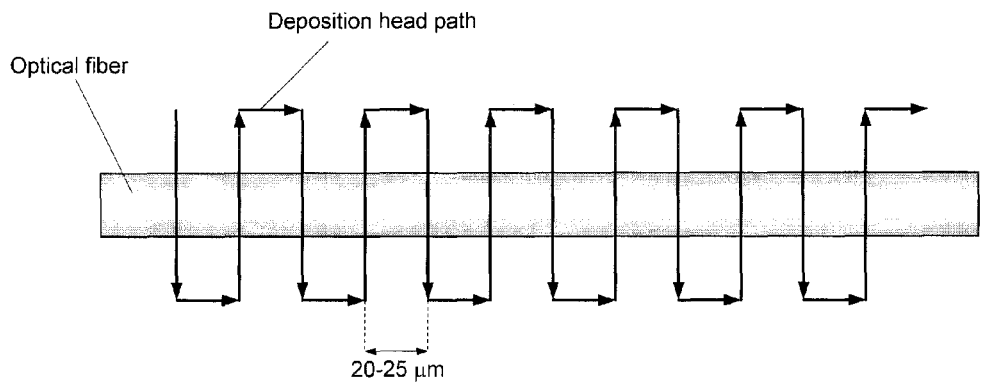
Figure 38: Path followed by the deposition head of LAMM relative to the optical fiber for the deposition of on-fiber silver thin films
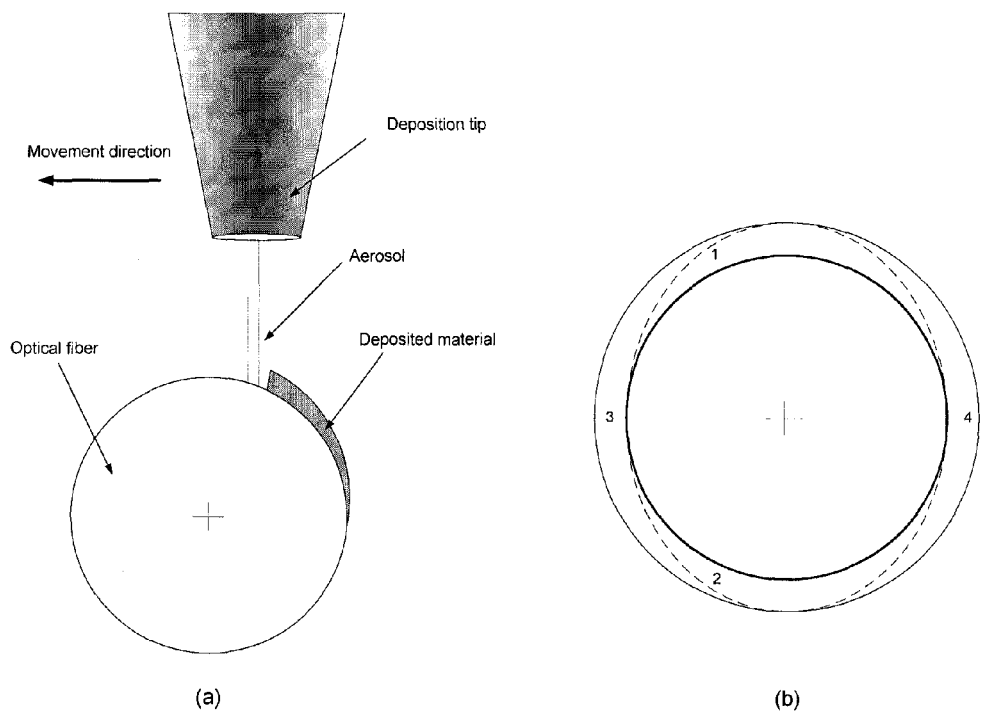
(a)          (b)
Figures 39 a and b: (a) Schematic diagram of the LAMM deposition tip and the optical fiber and (b) for
each set of depositions the fiber is rotated by 90°.

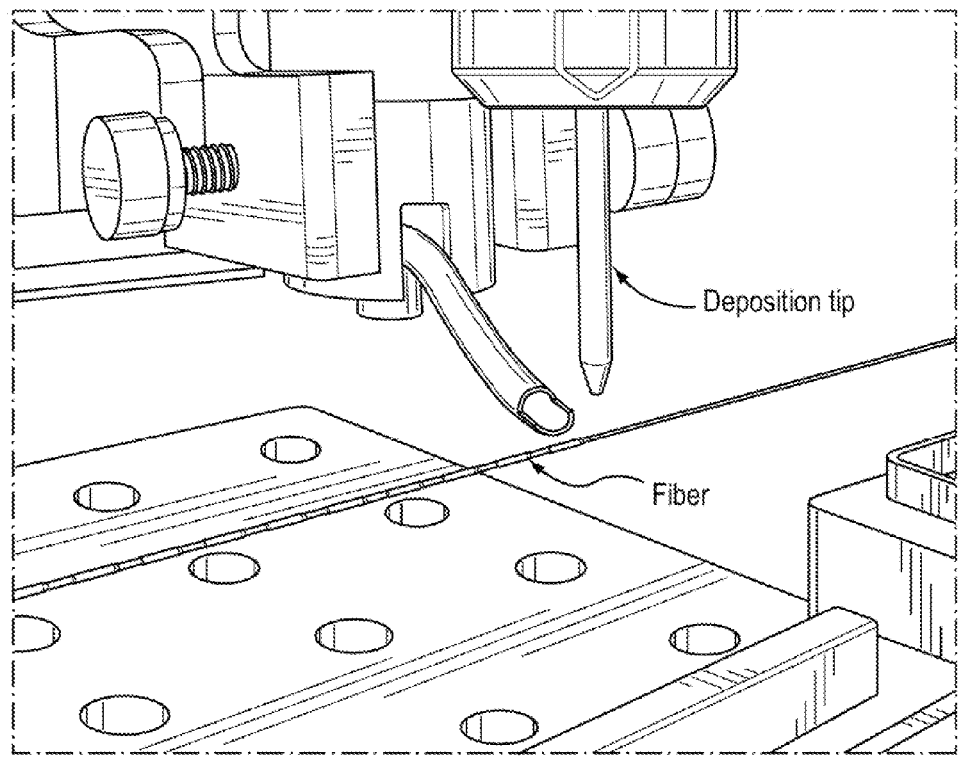
FIG. 40 LAMM deposition tip and the optical fiber during the deposition of on-fiber silver thin films
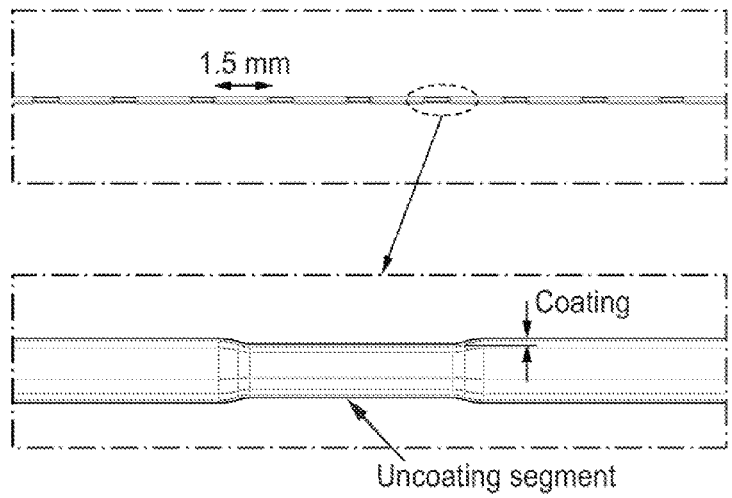
FIG. 41 Periodic silver thin films with a thickness of 9 μm deposited on an optical fiber

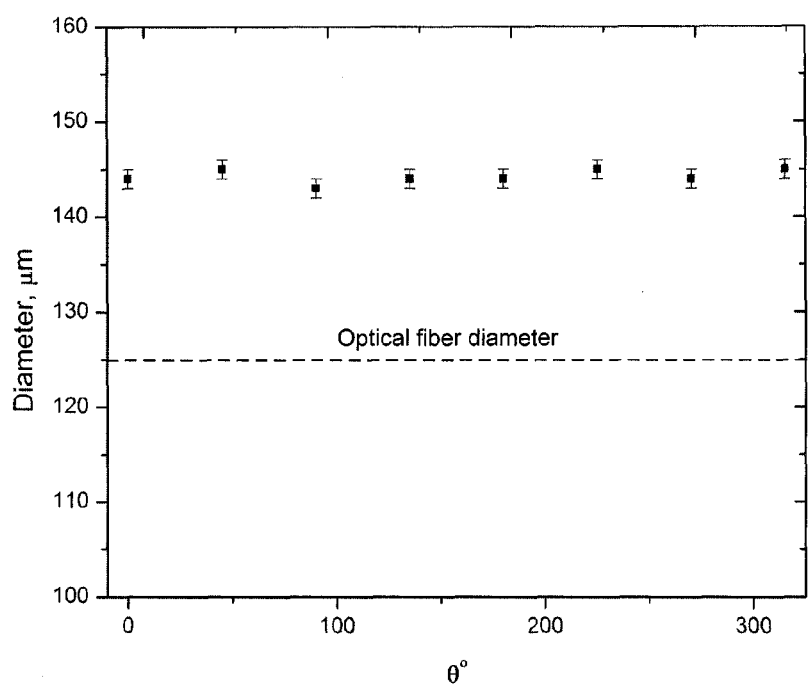
Figure 42: Distribution of the thickness of silver thin films deposited around the optical fiber

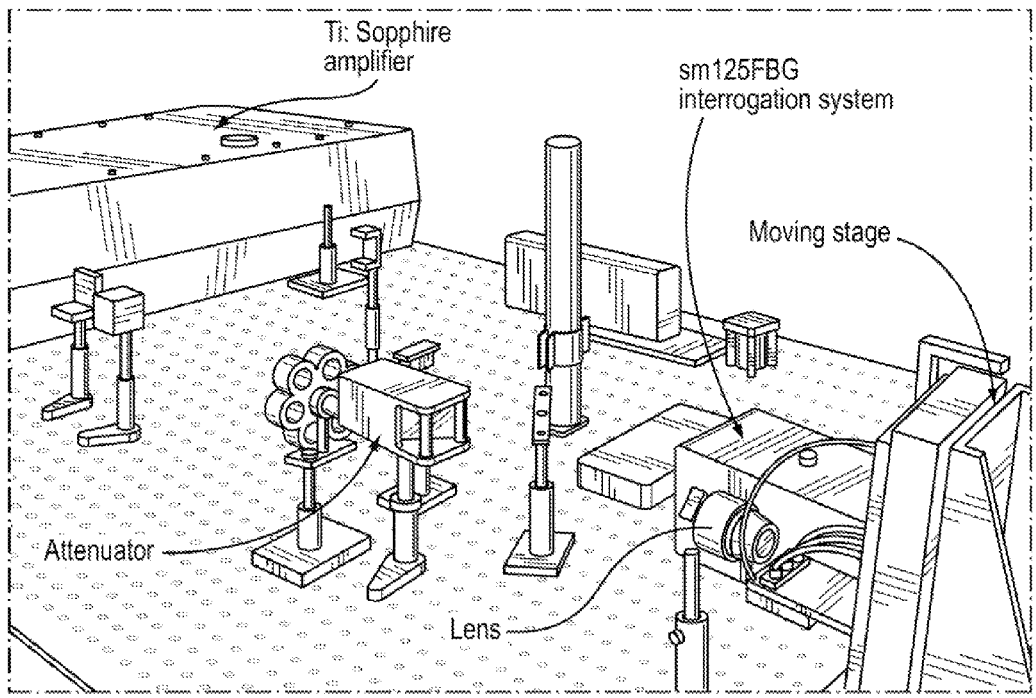
FIG. 43 Femtosecond laser workstation setup at LPRC, the University of Manchester, UK
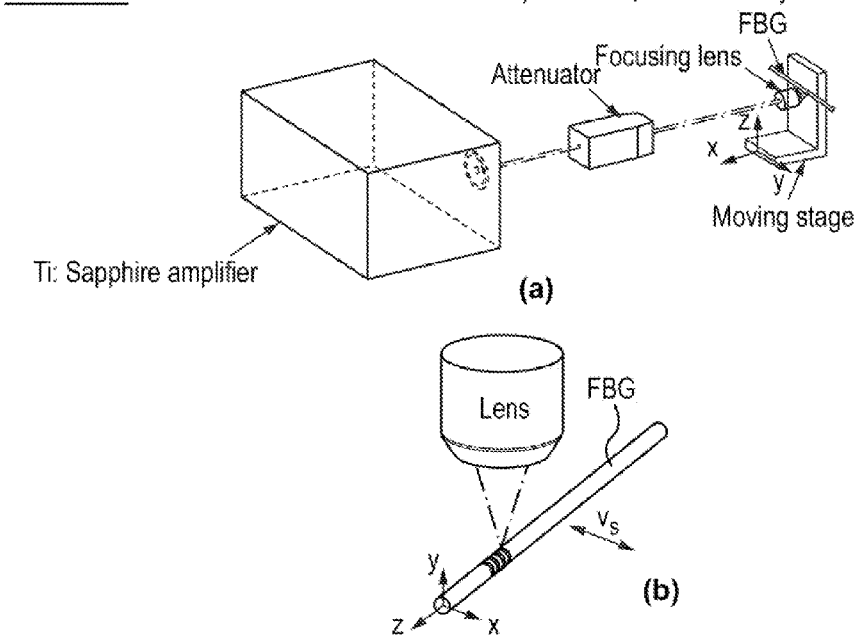
FIG. 44 (a) Schematic diagram of the femtosecond laser workstation setup and (b) femtosecond laser beam and FBG

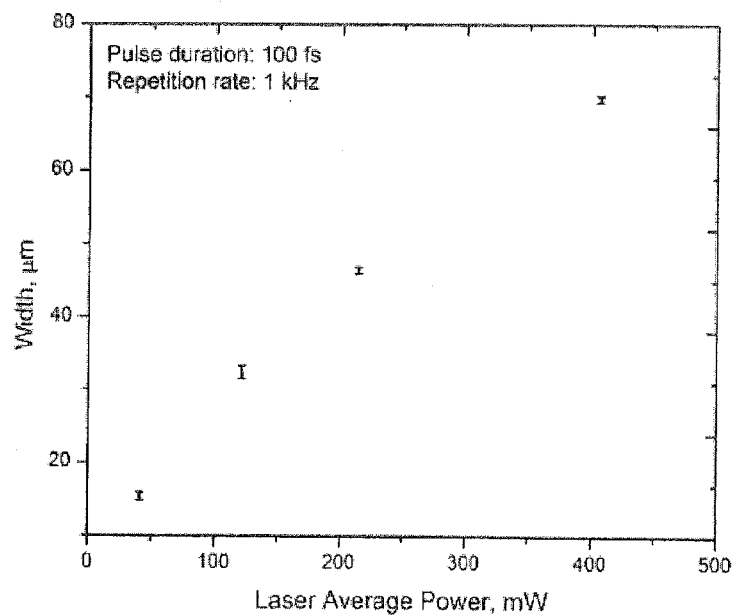
Figure 45: Micro-grooves width as a function of laser average power for laser scanning speed of 5 μm/s, inscribed on a planar silica substrate
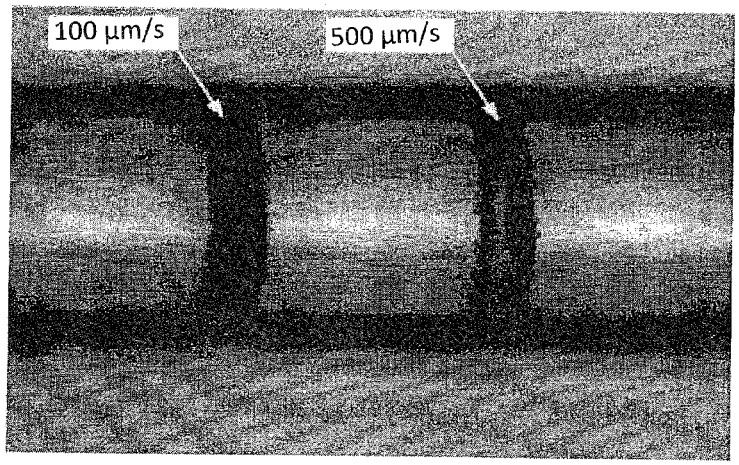
Figure 46: Effect of laser scanning speed on the surface quality of micromachined grooves on an optical fiber

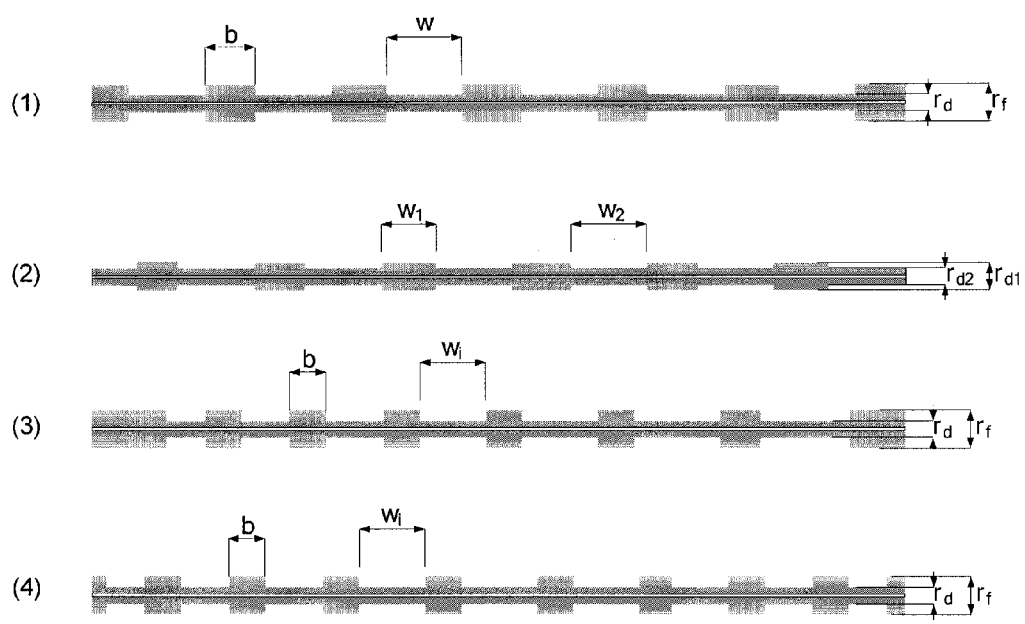
Figure 47: Diferent microcutting patterns on the outer surface of optical fiber to make superstructure FBGs for the simultanous measurment of two parameters

OPTICAL FIBER SENSOR AND METHODS OF MANUFACTURE

CROSS REFERENCE TO RELATED APPLICATIONS

This application claims the benefit of priority of U.S. Provisional Patent Application No. 61/213,796, filed Jul. 16, 2009, which is incorporated herein by reference in its entirety.

FIELD

The present disclosure relates generally to an optical fiber sensor and method of manufacturing an optical fiber sensor. More particularly, the present disclosure relates to an optical fiber sensor capable of simultaneously detecting and measuring more than one criteria at one or more predetermined locations on the optical fiber using a single data source, and a method of making such an optical fiber sensor.

BACKGROUND

Optical fiber sensors, specifically optical Fiber Bragg Gratings (FBG), are known in the art. FBG is a type of optical fiber whose spectral response is affected by applied strain and temperature. As a result, known FBGs can be used to measure a change in either strain or temperature. The unique features of optical fiber sensors, such as FBGs, have encouraged the use of optical fiber-based sensing devices These unique features of optical fiber sensors include light weight, small size, long-term durability, long-range linearity, robustness to electromagnetic disturbances, and resistance to corrosion. Despite the encouraging features, there are some limitations and challenges associated with prior art FBGs and their applications. One of the challenges associated with prior art FBGs is the coupling of the effects of strain and temperature in the optical response of the sensors which affects the reliability and accuracy of the measurements.

It is desirable to provide an optical fiber sensor that is capable of simultaneously detecting and measuring more than one criteria at one or more locations on the optical fiber using a single data source.

SUMMARY

It is an object of the embodiments in the present disclosure to obviate or mitigate at least one disadvantage of previous optical fiber sensors.

This disclosure describes modeling, design, and fabrication of new FBG-based sensing devices. These sensing devices can be used for structural measurements, failure diagnostics, thermal measurements, pressure monitoring, as well as in medical devices, for example, those used for diagnosing cancer. Other applications such as structural health monitoring of aerospace structures, bridge structures, buildings, downhole measurements in oil and gas wells, and seismic vibration measurements are possible.

Making FBGs sensitive to the index of refraction and keeping their thermal sensitivity intact enables optical sensors with the capability of the simultaneous measurement of concentration and temperature. Considering the unique features of FBGs, embedding of the sensors in metal parts for in-situ load monitoring is also possible. Several industries such as machining tools, aerospace, and automotive industries can benefit from this technology.

Laser microfabrication methods are implemented for the fabrication of the devices. Two approaches are adopted for the development of the FBG-based sensing devices: the additive method and the subtractive method. The additive method deals with the deposition of on-fiber metal thin films, and the subtractive method is based on the selective removal of material from the periphery of optical fibers.

To address the temperature-strain coupling in FBGs, Superstructure FBGs (SFBG) with on-fiber metal thin films are designed and fabricated. These SFBGs have the capability of measuring strain and temperature simultaneously. An opto-mechanical model of FBGs for thermal and structural monitoring was developed to design the sensing devices and analyze the performance of the sensors. The model is derived from the photo-elastic and thermo-optic properties of optical fibers. The developed model can be applied to predict the optical responses of a FBG exposed to structural loads and temperature variations with uniform and non-uniform distributions. The model is also extended to provide optical responses for superstructure FBGs, in which a secondary periodicity is induced in the index of refraction along the optical fiber. The design of the sensor with on-fiber thin films is carried out by using the developed opto-mechanical model of FBGs.

A laser-based Direct Write (DW) method, called Laser-Assisted Maskless Microdeposition (LAMM), can be used to selectively deposit thin films on optical fibers and fabricate the superstructure FBGs. To attain thin films with premium quality, a characterization scheme is designed to develop the geometrical, mechanical, and microstructural properties of the thin films in terms of the LAMM process parameters. It is anticipated that any direct writing, direct deposition, direct printing, layer-by-layer deposition, direct additive manufacturing, or layered manufacturing method, whether laser based or not, can be used to form the films on the optical fibers.

Femtosecond laser micromachining and Hydrofluoric acid etching can also be successfully implemented as a subtractive method for the sensor fabrication. For this purpose, periodic micro-grooves are inscribed in the cladding of regular FBGs so as to increase their sensitivity to the concentration of their surrounding environment while keeping their thermal sensitivity intact. This type of sensor has the potential for applications in biomedical research, in which the in-situ measurement of the properties of biological analytes is required.

Another application of the FBG sensors described in the present disclosure is that they can be embedded in metal parts for structural health monitoring using low temperature embedding processes. In this regard, the opto-mechanical model is extended to predict the optical response of the embedded FBGs. The embedding process involves low temperature casting, on-fiber thin film deposition, and electroplating methods.

In a first aspect, the present disclosure provides an optical fiber sensor wherein the optical fiber sensor is capable of simultaneous detection of more than one criteria at each of one or more predetermined locations on the optical fiber sensor.

In one case, the sensor is capable of simultaneously detecting two criteria, the two criteria selected from the group consisting of temperature and strain, temperature and stress, temperature and pressure, temperature and force, temperature and level of hydrogen, and temperature and humidity.

In another case, the optical fiber is a Fiber Bragg Grating optical fiber and a plurality of coatings are positioned around a periphery of the optical fiber.

In another case, the optical fiber is a Fiber Bragg Grating optical fiber having a first end connected to a spectrum signal analyzer which reads only reflected light.

In another case, the plurality of coatings are equally spaced along a length of the optical fiber.

In another case, the plurality of coatings are non-equally spaced along a length of the optical fiber.

In another case, the plurality of coatings comprises a first set of coatings and a second set of coatings, the first set of coatings being equally spaced along a length of the optical fiber, and the second set of coatings being non-equally spaced along the length of the optical fiber.

In another case, the plurality of coatings are a film having a thickness of up to about 200 µm.

In another case, the plurality of coatings are a film having a thickness of about 9 µm.

In another case, the plurality of coatings are a conductive element selected from the group consisting of titanium, silver, gold, platinum, zinc, aluminum, magnesium, copper, iron, nickel, chromium, palladium, lead and combinations thereof.

In another case, the plurality of coatings are silver.

In another case, the plurality of coatings are polymer material.

In another case, the plurality of coatings have a length of approximately 1.5 mm and a space between adjacent coatings is 0.5 mm.

In another case, the plurality of coatings have a length of up to one-third of a length of a grating of the optical fiber sensor, and a space between adjacent coatings is up to one-third of the length of the grating.

In another case, the optical fiber has a plurality of bands of a reduced radius around a surface of the optical fiber.

In another case, the bands have a depth of up to 40 µm from the surface of the optical fiber to a bottom of the bands.

In another case, each of the plurality of bands have a length of up to one-third of a length of a grating of the optical fiber sensor, and a space between adjacent bands is up to one-third of the length of the grating In another case, the plurality of bands are equally spaced along a length of the optical fiber.

In another case, the plurality of bands are non-equally spaced along a length of the optical fiber.

In another case, the plurality of bands comprises a first set of bands and a second set of bands the first set of bands being equally spaced along a length of the optical fiber, and the second set of bands being non-equally spaced along the length of the optical fiber.

In another case, the more than one criteria are selected from the group consisting of temperature and strain, temperature and force, temperature and stress, temperature and pressure, and temperature and liquid concentration In another aspect, the disclosure provides a method of making an optical fiber sensor capable of simultaneously detecting more than one criteria at one or more predetermined locations, the method comprising: applying at least one thin coating onto a non-planar surface of the optical fiber.

In one case, the coating is applied by a procedure selected from the group consisting of direct writing, direct deposition, direct printing, layer-by-layer deposition, direct additive manufacturing, solid freeform fabrication, and layered manufacturing.

In another case, the procedure is laser-based.

In another case, the coating is applied by laser direct writing.

In another case, the laser direct writing is laser-assisted maskless micro-deposition.

In another case, the more than one criteria are selected from the group consisting of temperature and strain, temperature and stress, temperature and pressure, temperature and level of hydrogen, and temperature and humidity In yet another aspect, the disclosure provides a method of making an optical fiber sensor capable of simultaneously detecting more than one criteria at one or more predetermined locations, the method comprising removing material from a surface of the optical fiber.

In one case, the coating of material is removed by femtosecond laser etching of the surface of the optical fiber.

In another case, the coating of material is removed by selectively applying Hydrofluoric acid to the surface of the optical fiber.

In another case, the more than one criteria are selected from the group consisting of temperature and strain, temperature and force, temperature and stress, temperature and pressure, and temperature and liquid concentration.

In another case, the material is removed from a circumference of the optical fiber to form a plurality of circumferential bands along the optical fiber, the bands being formed having a depth of up to 40 µm from the surface of the optical fiber.

In another case, the bands have a length of up to one third of a length of a grating of the optical fiber, and each band is spaced from an adjacent one of said bands at a distance of up to one third of the length of the grating.

Other aspects and features of the present disclosure will become apparent to those ordinarily skilled in the art upon review of the following description of embodiments in conjunction with the accompanying figures.

BRIEF DESCRIPTION OF THE DRAWINGS

Embodiments of the present disclosure will now be described, by way of example only, with reference to the attached Figures.

FIG. 1 shows the graph of the reflection spectrum of superstructure FBGs;

FIG. 2 shows an optical fiber with periodic metallic coatings positioned at spaced intervals along the optical fiber and the effect on the average index of refraction;

FIG. 3 shows optical fibers with different patterns of periodic metallic coatings with general period, quantity, and coating thickness. The figure also shows the corresponding reflection of spectrum of the associated superstructure FBG;

FIG. 4 shows an optical fiber and metallic coating in cylindrical co-ordinates system;

FIG. 5 shows the variations of the parameter $\hat{K}$ along the optical fiber at different tensile forces;

FIG. 6 shows the variations of the parameter $\hat{K}$ along the optical fiber at different temperatures;

FIG. 7 shows the geometrical dimensions of periodic silver films deposited on FBG;

FIG. 8 shows the graphs of the reflection spectra of SFBG at different loads;

FIG. 9 shows the graphs of reflectivity as a function of force for SFBG;

FIG. 13 shows the graphs of Bragg wavelength as a function of temperature for SFBG;

FIG. 14 shows a test set-up for structural and thermal loading of a superstructure FBG;

FIG. 15 shows a graph indicating FBG reflectivity before and after the fabrication of silver films;

FIG. 16 shows a graph indicating reflectivity as a function of Bragg wavelength in a thermal cycle;

FIG. 17 shows a graph indicating Bragg wavelength as a function of temperature;

FIG. 18 shows an illustration of the strain components in the coated and uncoated segments of the superstructure FBG as a function of temperature;

FIG. 23 shows a graph indicating Bragg wavelength as a function of temperature for superstructure FBG under tensile force and temperature;

FIG. 24 shows typical characteristic curves for SFBG to measure strain and temperature;

FIG. 25 shows a Laser-Assisted Maskless Microdeposition ("LAMM") setup for the deposition of silver films on FBG's;

FIG. 26 shows a rotational stage for the installation of optical fiber;

FIG. 27 shows the sintering mechanism of nanoparticle;

FIG. 28 shows typical deposition patterns using the LAMM system;

FIG. 29 shows the profiling images of the deposition patterns in FIG. 28;

FIG. 30a shows a microstructure of silver films sintered at 1.35 W taken by a Field Emission Scanning Electron Microscope ("FE-SEM") at 5 kX;

FIG. 30b shows a microstructure of silver films sintered at 1.35 W taken by a FE-SEM at 20 kX;

FIG. 31a shows a microstructure of silver films sintered at 3.28 W taken by a Field Emission Scanning Electron Microscope ("FE-SEM") at 5 kX;

FIG. 31b shows a microstructure of silver films sintered at 3.28 W taken by a FE-SEM at 20 kX;

FIG. 32 shows the XRD spectra of silver thin films;

FIG. 33 shows the magnified peak of XRD spectrum corresponding to (200) plates;

FIG. 34 shows the nanoindentation profile in the silver thin film;

FIG. 35 shows the graphs of the load-displacement in nanoindentation test;

FIG. 36 shows the hardness of silver thin films a function of laser power;

FIG. 37 shows the modulus of elasticity of the silver thin films as a function of laser power;

FIG. 38 shows the LAMM deposition paths on the optical fiber;

FIG. 39a shows a cross-sectional view of an optical fiber with a deposition nozzle in the process of depositing film on the optical fiber;

FIG. 39b shows a cross-sectional view of the optical fiber in FIG. 5a, after deposition of film, and whereby the optical fiber was rotated by 90 degrees to achieve a uniform coating thickness;

FIG. 40 shows the LAMM deposition head during the deposition of periodic silver thin films on an optical fiber;

FIG. 41 shows a FBG having periodic silver coatings;

FIG. 42 shows the diameter of the thin films deposited on the optical fiber; and FIG. 43 shows a femtosecond laser workstation setup;

FIG. 44a shows a schematic diagram of the femtosecond laser workstation shown in FIG. 43;

FIG. 44b shows a femtosecond laser beam and FBG;

FIG. 45 shows a graph of the width of micro-grooves as a function of laser average power for laser scanning speed of 5 um/s, inscribed on a planar silica substrate;

FIG. 46 shows an optical fiber with micromachined grooves etched therein; and

FIG. 47 shows four optical fibers each having a plurality of grooves with different spacing between grooves and groove depths.

DETAILED DESCRIPTION

Figure 10:
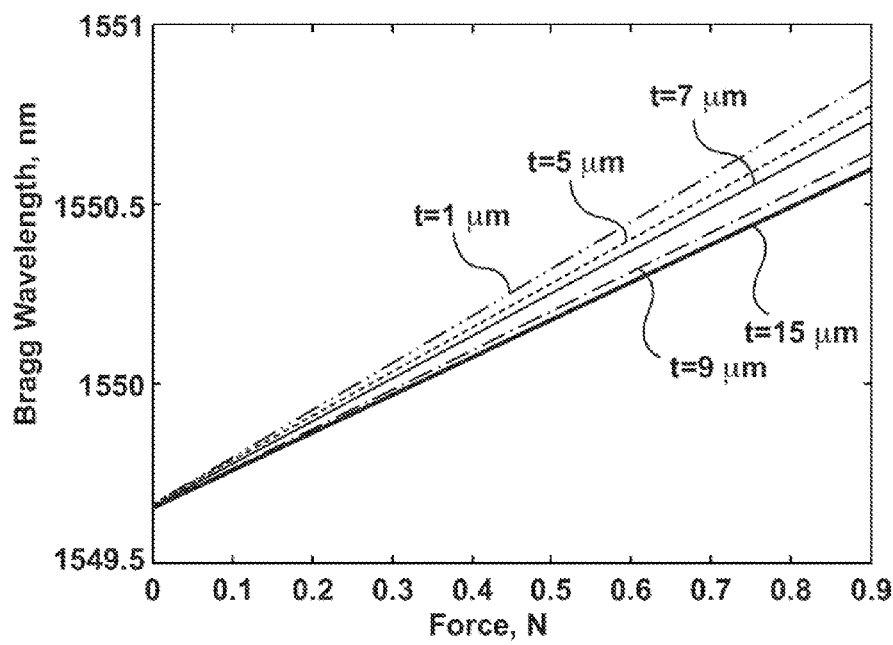
FIG. 10 shows the graphs of Bragg wavelength as a function of force for SFBG.

Generally, the present disclosure provides an optical fiber sensor capable of simultaneously detecting more than one physical criteria at one or more predetermined locations, sometimes referred to as specific locations, on the optical fiber, and a method of making such an optical fiber sensor.

Fiber Bragg Gratings (FBGs), which have a modulation of the index of refraction with a period of L, along the core of optical fibers have been widely used for sensing physical parameters and, filtering. As sensors, FBGs are used for the measurement of force, stress, strain, pressure and temperature. These capabilities initiate from the optical sensitivity of FBGs to stain and temperature. Compared to conventional electric and electromagnetic devices, FBGs are quite advantageous. They have light weight, small size, long-term durability, long-range linearity, and robustness to external electromagnetic disruptions.

A superstructure FBG (SFBG) is a type of FBG in which the modulation of the index of refraction is not uniform, but varies periodically (with a larger period than the initial grating) along the fiber. This produces periodically spaced sidebands, as shown in FIG. 1, in the reflectivity spectrum having a broad range of applications in fiber lasers, tunable filters, and multi-parameter sensors. The long periodic variations of the index of refraction can be introduced in FBGs during the grating inscription using UV radiation. Although these SFBGs can be used for the above-mentioned applications, the intensity of the sidebands is generally fixed and cannot be tuned. In addition, for multi-parameter sensing, the transmission signal is captured and analyzed, rather than the reflection spectrum. As described further herein, the novel concept of tunable superstructure FBGs can be realized by, for example, the fabrication of periodic metallic films on optical fibers.

In SFBGs, the modulations of the index of refraction vary periodically along the fiber axis with a longer period (typically larger than 100 μm) than that of the grating. The long-period variations of the index of refraction cause the formation of equally spaced sidebands in the reflection spectrum of the SFBG.

The concept of SFBG can also be realized by the deposition of periodic metal films on FBGs, as shown in FIG. 2. In a SFBG with periodically deposited on-fiber thin films, a periodic distribution of strain is induced along the grating, when the fiber is exposed to axial force (F) or thermal heating/cooling (ΔT). This is due to the differences in the geometries and the thermal expansions of the films and the optical fiber. The periodic distribution of the strain components along the grating causes the periodic variations of the average index of refraction ($\overline{\Delta n}$) (due to photo-elastic effect). In addition to the index of refraction, the grating pitch (Λ) varies periodically along the fiber. The sideband spacing in a FBG, coated with metal films with period of Γ is derived from the phase matching condition:

$$\Delta\lambda = \frac{\lambda_B^2}{2n_{eff}\Gamma} \quad (1)$$

The fabrication of metallic thin films on FBGs is used for dispersion compensation, tunable Bragg gratings, and sensitivity enhancement at cryogenic temperatures. Electrowinning, sputtering, electron beam evaporation, and electroplating techniques are conventional methods that are employed for the deposition of, for example, Ti, Ag, Au, Pt, Zi, and Cu films onto optical fiber. It is contemplated that polymeric material could also be used as a film coating.

A variety of superstructure FBGs can be produced by changing the period, length, materials and thickness of the deposited patterns (FIG. 3). Such superstructure FBGs produced in this way will have a special reflecting spectrum enabling a variety of multi-parameter measurements. The design parameters for these types of superstructure FBGs are the geometrical parameters of the coatings including $t, t_1, t_2, r_f, r_c, r_{c1}, r_{c2}, r_{c3}, b, w, w_1, w_2, w_i$ and the mechanical properties of the coating materials, i.e. modulus of elasticity and the coefficient of thermal expansion.

A non-exhaustive list of anticipated examples for the multiparameter measurements are:
1. Strain and temperature;
2. Stress and temperature;
3. Force and temperature;
4. Pressure and temperature;
5. Level of Hydrogen ($H_2$) and temperature (using, for example, Palladium coating material);
6. Gas & temperature sensor: any appropriate coating material that expands at the presence of the gas and applies strain on the fiber; and
7. Relative Humidity and temperature: any appropriate coating material (e.g. moisture sensitive polymer) that expands at the presence of moisture and humidity and applies mechanical strain.

In a first embodiment, a superstructure FBG with multi-parameter sensing capability is formed by the deposition of periodic metallic films on conventional FBGs. In one example method, the metallic films are fabricated using Laser-Assisted Maskless Microdeposition (LAMM) technique, which is a type of laser direct write (LDW) method. Compared to conventional coating techniques, maskless direct write methods are generally faster and more flexible. In LAMM, a metal, e.g. silver, nanoparticle suspension is used for layer-by-layer deposition, in which the nanoparticles are sintered using a laser beam and/or a furnace after deposition.

The periodically spaced sidebands in the reflection spectrum of SFBG have a broad range of applications in fiber lasers and tunable filters. In contrast to superstructure FBGs fabricated by UV exposure, the reflectivity of the sidebands in SFBGs with on-fiber films can be tuned by changing temperature and force. The concept of tunable SFBG by the fabrication of metal films on optical fibers has been elaborated on in the paper of Ahuja et al., "Tunable Single Phase-Shifted and Superstructure Gratings Using Microfabricated On-Fiber Thin Film Heaters," Optics Communications, vol. 184, pp. 119-125, 2000, the contents of which are incorporated herein by reference. Ahuja, et al. propose tunable SFBGs for wavelength-division multiplexing, optical sensing, and fiber lasers. In their work, thin films of gold with periodic variable diameters were deposited on a pre-deposited on-fiber titanium thin film by using electron beam evaporation. Ahuja showed that joule heating causes a periodic distribution of temperature along the fiber. This creates sidebands whose reflectivities are tuned by electric current. Although Ahuja discusses depositing thin films on optical fibers, Ahuja fails to teach applying films in a pattern as described herein to achieve the same results described herein.

From the sensing point of view, SFBGs with periodic metal coatings can be used for simultaneous parameter measurements, which eliminates the inherent limitations of FBGs in the thermal and structural measurements. The intensity of the sidebands generated in SFBGs is regulated by the applied temperature and force on the optical fiber. The intensity of the sidebands combined with the Bragg wavelength shift can be used to discriminate the coupled effects of temperature and strain. UV induced SFBGs have been used for multi-parameter sensing. In the work of Guan, et al. "Simultaneous Strain and Temperature Measurement Using a Superstructure Fiber Bragg Grating" IEEE Photonics Technology Letters, vol. 12, no. 6, pp. 675-677, 1997, the contents of which are incorporated herein by reference, the transmission spectrum of a UV-exposed SFBG was used for the simultaneous measurement of strain and temperature. The measurements were based on the analysis of the attenuation bands generated by cladding mode couplings. However, UV-exposed SFBG is not advantageous for reasons described herein and requires the capture of both reflection and transmission of UV rays. Thus sensing equipment is disadvantageously required to be connected at both ends of the SFBG with UV-exposed SFBG. In the present optical fiber sensor, only one end of the fiber needs to be connected to sensing equipment, such as a spectrum signal analyzer, which reads only reflected light.

In the present disclosure, the LAMM process was adopted for the fabrication of on-fiber thin films.

To design the SFBGs with multi-parameter sensing capabilities, an opto-mechanical model is developed. The model consists of two components: (1) structural model of SFBGs to find the state of stress and strain in optical fibers, and (2) opto-mechanical model consisting of the photo-elastic and thermo-optic effects to find the reflection spectrum of SFBGs.

For the structural modeling of SFBGs exposed to force and temperature variations, it is assumed that the optical fiber is uniformly heated by $\Delta T$ and is exposed to an axial tensile force of F. The approach is similar to the modeling of thick-wall cylinders under structural loading and temperature variations. FIG. 4 demonstrates the coated segment of the optical fiber in cylindrical coordinates $(r, \theta, z)$. It is assumed that the optical fiber with a diameter of $r_f$ is coated with a layer with a thickness of $t = r_c - r_f$.

The displacement component in q direction (v) is neglected, because of the symmetry, and the dependency of the radial and axial displacements (u,w) on z is considered to be small at the points far from the ends. At these points, the shear components are also zero because of the symmetry. The strain-displacement relations are written as $$e_{rr} = \frac{du}{dr} \quad (2)$$
$$e_{\theta\theta} = \frac{u}{r}$$

As a result, $e_{rr}$ and $e_{\theta\theta}$ are interrelated as $$\frac{d}{dr}(re_{\theta\theta}) = e_{rr} \tag{3}$$

From the equilibrium conditions, the radial and tangential stress components, $\sigma_{rr}$ and $\sigma_{\theta\theta}$, are related as $$r\frac{d\sigma_{rr}}{dr} = \sigma_{\theta\theta} - \sigma_{rr} \tag{4}$$

which yields $$\frac{d}{dr}(r\sigma_{rr}) = \sigma_{\theta\theta} \tag{5}$$

The stress-strain-temperature relations are written as $$\begin{bmatrix} e_{rr} \\ e_{\theta\theta} \\ e_{zz} \end{bmatrix} = \frac{1}{E}\begin{bmatrix} 1 & -v & -v \\ -v & 1 & -v \\ -v & -v & 1 \end{bmatrix}\begin{bmatrix} \sigma_{rr} \\ \sigma_{\theta\theta} \\ \sigma_{zz} \end{bmatrix} + \alpha\Delta T \tag{6}$$

where n is the Poisson's ratio, E is the modulus of elasticity, and $\alpha$ is the coefficient of thermal expansion. By integrating (3) and (5) and using (6), the stress components in the optical fiber and the coating are obtained as follows:

$$\sigma_{rr}^f = \frac{-\alpha_f E_f}{2(1-v_f)}\Delta T + C_1^f \tag{7}$$

$$\sigma_{\theta\theta}^f = \frac{-\alpha_f E_f}{2(1-v_f)}\Delta T + C_1^f$$

$$\sigma_{rr}^c = \frac{-\alpha_c E_c}{2(1-v_c)}\Delta T + C_1^c\left(1 - \frac{r_f^2}{r^2}\right) + \frac{C_2^c}{r^2}$$

$$\sigma_{\theta\theta}^c = \frac{-\alpha_c E_c}{2(1-v_c)}\Delta T + C_1^c\left(1 - \frac{r_f^2}{r^2}\right) - \frac{C_2^c}{r^2}$$

where $C_1^c$, $C_1^f$, and $C_2^c$ are integration constants and the superscripts f and c are associated with the optical fiber and the coating, respectively. Considering the following boundary conditions, $$e_{zz}^f = e_{zz}^c \tag{8}$$

$$\sigma_{zz}^f A_f + \sigma_{zz}^c A_c = F$$

$$\sigma_{rr}^c(r_c) = 0$$

$$e_{\theta\theta}^f(r_f) = e_{\theta\theta}^c(r_f)$$

$$\int_{r_f}^{r_c} \sigma_{\theta\theta}^c dr = \int_0^{r_1} \sigma_{\theta\theta}^f dr$$

$\sigma_{zz}^f$, $\sigma_{zz}^c$, $C_1^c$, $C_1^f$, and $C_2^c$ are obtained, which are substituted in (7) and (6) to find the strain components.

The results of the structural modeling are used in the opto-mechanical model to find the anisotropic index of refraction by using (9), and the modified effective mode index of refraction by using (10) in the coated and uncoated segments of the optical fiber.

$$\Delta n_1 = -\frac{n_1^3}{2}(p_{11}e_1 + p_{12}(e_2+e_3)) + \left(\frac{\partial n}{\partial T}\right)\Delta T + \frac{n_1^3}{2}(p_{11}+2p_{12})\alpha\Delta T \tag{9}$$

$$\Delta n_2 = -\frac{n_2^3}{2}(p_{11}e_2 + p_{12}(e_1+e_3)) + \left(\frac{\partial n}{\partial T}\right)\Delta T + \frac{n_2^3}{2}(p_{11}+2p_{12})\alpha\Delta T$$

$$\Delta n_3 = -\frac{n_3^3}{2}(p_{11}e_3 + p_{12}(e_1+e_2)) + \left(\frac{\partial n}{\partial T}\right)\Delta T + \frac{n_3^3}{2}(p_{11}+2p_{12})\alpha\Delta T$$

$$\Delta n_4 = -n_4^3\frac{(p_{11}-p_{12})}{4}e_4$$

$$\Delta n_5 = -n_5^3\frac{(p_{11}-p_{12})}{4}e_5$$

$$\Delta n_6 = -n_6^3\frac{(p_{11}-p_{12})}{4}e_6$$

$$\Delta n_{eff1} = \tag{10}$$

$$-\frac{n_{eff1}^3}{2}(p_{11}e_2 + p_{12}(e_1+e_3)) + \frac{\partial n}{\partial T}\Delta T + \frac{n_{eff1}^3}{2}(p_{11}+2p_{12})\alpha\Delta T$$

$$\Delta n_{eff2} = -\frac{n_{eff2}^3}{2}(p_{11}e_3 + p_{12}(e_1+e_2)) +$$

$$\frac{\partial n}{\partial T}\Delta T + \frac{n_{eff2}^3}{2}(p_{11}+2p_{12})\alpha\Delta T$$

where $e_1$, $e_2$, and $e_3$ are strain components and $p_{11}$ and $p_{12}$ are the photo-elastic constants.

Afterwards, the coupled-mode equations are solved to obtain the spectral response of SFBG. The coupled mode equation is written as $$\frac{d\rho(z)}{dz}iK_{AC}\rho^2 + 2i\left(\frac{2\pi n_{eff}}{\lambda} - \frac{\pi}{\Lambda} - \frac{1}{2}\frac{d\Phi}{dz} + K_{dc}\right)\rho + iK_{AC} \tag{11}$$

which is in the form of the Riccati equation. $\rho$ is the ratio of the amplitude of the reflected propagation mode to the transmitted propagation mode. $\Phi$ is the grating chirp and $K_{dc}$ and $K_{AC}$ are the coupling coefficients. z is along the optical fiber axis. The reflectivity at each wavelength is $(r(\lambda))$ and is obtained from $$r(\lambda) = |\rho(-L/2)|^2 \tag{12}$$

The boundary condition is $$\rho(L/2) = 0 \tag{13}$$

where L is the grating length.

The Riccati ODE (11) can be solved by direct integration. A 4th-order Runge-Kutta algorithm was developed for this purpose in MATLAB. The simulation results are presented to investigate the effects of different parameters on the optical response of the SFBG sensor. The optical constants for the simulations are listed in Table 1. The values are obtained for the FBGs supplied from external suppliers.

The coefficient $\hat{K} = 2\pi n_{eff}/\lambda - \pi/\Lambda - d\Phi/2dz + K_{dc}$ in (11) is plotted along a FBG at different forces and temperatures at the wavelength of 1550 nm in FIG. 5 and FIG. 6. It is assumed that the original grating is Gaussian apodized. The graphs are obtained for the periodically spaced on-fiber silver coatings with a thickness of approximately 9 μm and a period of 2 mm, as shown in FIG. 7. It is assumed that there are seven silver films on a 14 mm long grating, and the length of coated segments is 1.5 mm.

As shown in FIG. 5 and FIG. 6, $\hat{K}$ changes with the same period as the thin films, and its amplitude increases as force and temperature increase.

When FBG is under tensile force F, $\hat{K}$ in the coated segments of the optical fiber is less than that in the uncoated segments due to the larger strain in the uncoated segments.

As a result of the temperature increase, $\hat{K}$ in the coated segments is larger than that of the uncoated segments. This is attributed to larger strain components in the coated segments of the fiber due to the differences in the coefficients of thermal expansions.

TABLE 1

Modeling constants

| Parameter | Value |
| --- | --- |
| $E_{silica}$ | 73 GPa |
| $E_{fiber}$ | 83 GPa |
| $n_{eff}$(initial) | 1.44405 |
| $p_{11}$ | 0.113 |
| $p_{12}$ | 0.252 |
| $\Delta n$ | $1 \times 10^{-5}$ |
| $v_f$ | 25 |
| $\Lambda$ (nm) | 537 |
| $\partial n / \partial T$ | $1.2 \times 10^{-5}$ |
| L (mm) | 14 |

FIG. 8 shows the reflection spectra of the SFBG as a function applied axial loads for 5, 7, and 9 µm silver film thicknesses. The simulations were run for the SFBG design shown in FIG. 7. The silver films are 1.5 mm long with a period of 2 mm. FIG. 9 and FIG. 10 show the reflectivity of the first upper sideband and the Bragg wavelength of SFBG as functions of the applied axial force at different film thicknesses. Table 2 contains the Bragg wavelength sensitivity to axial load for different film thicknesses. As seen the sensitivity of the Bragg wavelength to the applied axial load decreases with increasing the film thickness. At the film thickness of 1 µm the sensitivity is 1.32 nm/N. The sensitivity is reduced to 1.05 nm/N at the thickness of 15 µm. Increasing the film thickness results in the reduction of the average strain along the grating which leads to the reduction of the sensitivity of the Bragg wavelength. The sensitivity of the sidebands reflectivity increases with thicker films; however, the trend of the variations of reflectivity with axial force is not linear. The film thickness manifests itself in the amplitude of the periodic variation of strain along the grating.

TABLE 2

Bragg wavelength sensitivity to axial force for different film thicknesses

| Film Thickness (µm) | Bragg Wavelength Sensitivity (nm/N) |
| --- | --- |
| 1 | 1.32 |
| 5 | 1.23 |
| 7 | 1.17 |
| 9 | 1.10 |
| 15 | 1.05 |

Figure 11:
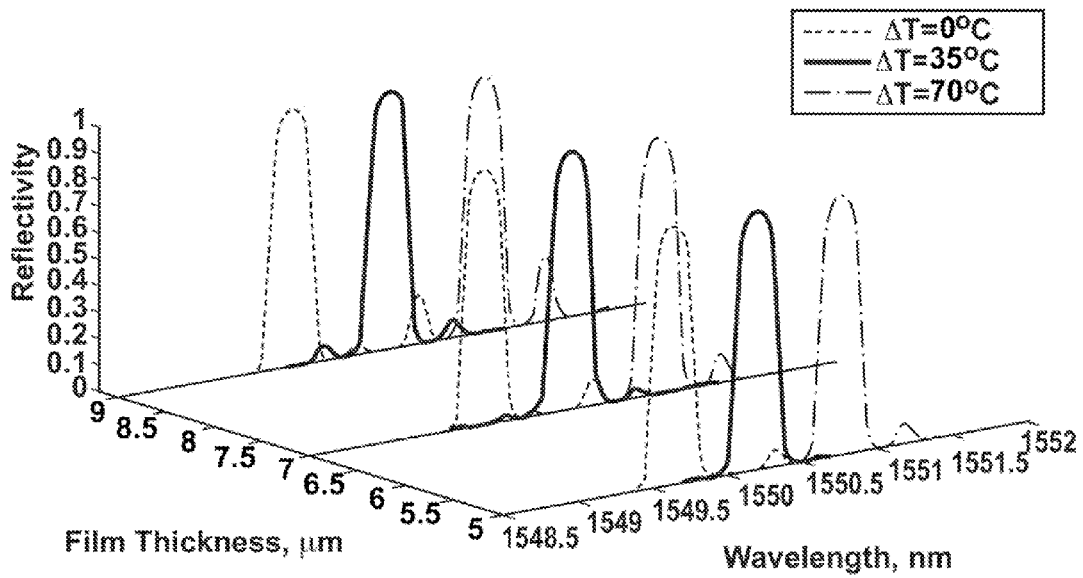
FIG. 11 shows the graphs of the reflection spectra of SFBG at different temperatures.
Figure 12:
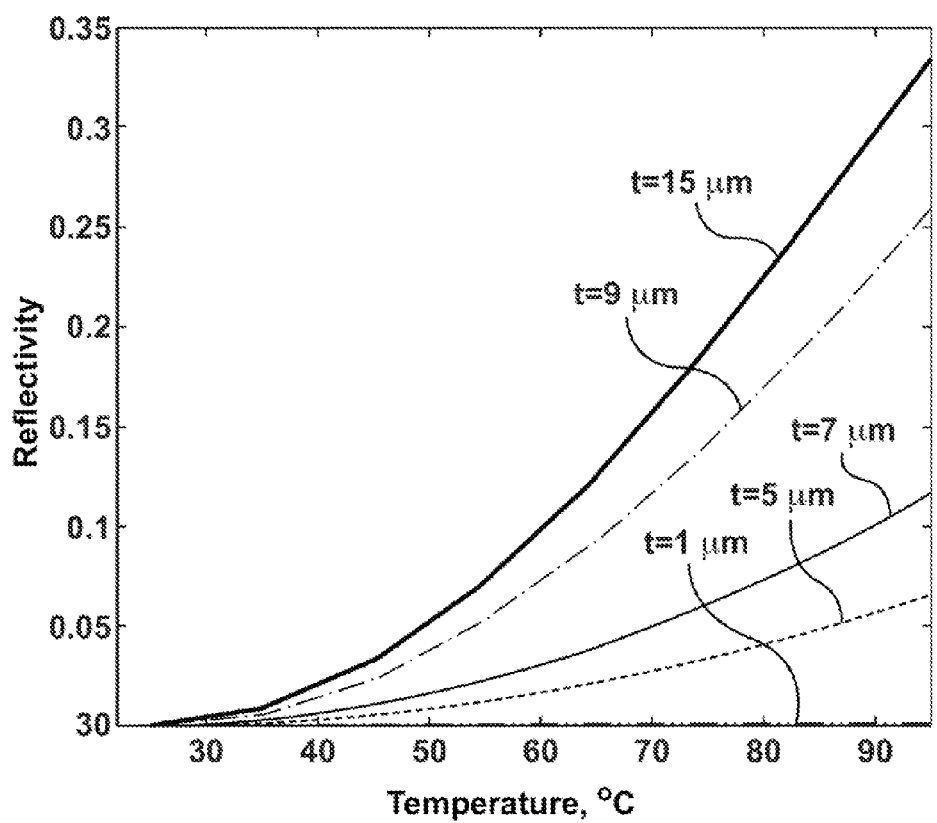
FIG. 12 shows the graphs of reflectivity as a function of temperature for SFBG.

The reflection spectra at various temperatures are plotted in FIG. 11. The Bragg wavelength vs. temperature and reflectivity vs. temperature graphs are plotted in FIG. 12 and FIG. 13. Table 3 summarizes the Bragg wavelength sensitivity to temperature for different film thicknesses. The thermal sensitivity of the Bragg wavelength to temperature increases from 14.2 pm/° C. at a film thickness of 1 µm to 18.8 pm/° C. at a film thickness of 15 µm. In addition, the sensitivity of the sidebands reflectivity increases in thicker films.

TABLE 3

Bragg wavelength sensitivity to temperature for different film thicknesses

| Film Thickness (µm) | Bragg Wavelength Sensitivity (pm/° C.) |
| --- | --- |
| 1 | 14.3 |
| 5 | 16.0 |
| 7 | 16.8 |
| 9 | 18.2 |
| 15 | 18.8 |

The tensile force and temperature can change the reflectivity of the sidebands as well as the Bragg wavelength. The sensitivity of the reflectivity of the sidebands to temperature and axial force is determined by the geometrical features of the periodic films. Thicker coatings increase the amplitude of the periodic variations of the index of refraction along the fiber which leads to higher sensitivities.

After the deposition and laser sintering of silver nanoparticles, residual stresses are generated in the coatings and the coated segments of the fiber. This changes the spectral response of the coated fiber at no-load conditions. In the current simulations, the residual stresses are ignored.

A SFBG was fabricated by depositing silver coatings on the outer surface of regular FBGs. The details of the deposition process using LAMM and the geometrical and the microstructural features of the silver films are discussed below. A FBG with a grating length of 14 mm was selected for the experiments, on which seven silver films with a duty cycle of ¾ were fabricated with the geometrical features depicted in FIG. 7.

For the analysis of the spectral response, the SFBG was loaded axially at different temperatures to study the effects of force and temperature simultaneously. For the axial loading, the optical fiber was mounted on a test rig which was connected to a motorized positioning stage, with a precision of 1 µm, and a load cell; as shown in FIG. 14. The grating segment of the FBG was placed in the proximity of a thermoelectric module in a chamber to control its temperature, measured by a thermocouple.

The reflection spectra of the FBGs were taken by sm125 FBG interrogation system (Micron Optics Inc., Atlanta, Ga., USA).

The reflection spectra of the SFBG before and after the fabrication of the silver films are exhibited in FIG. 15. A comparison of the two graphs signifies the presence of sidebands in the reflectivity after the deposition of the silver films. This is attributed to the formation of residual stresses in the optical fiber after the agglomeration and sintering of the nanoparticles. Sintering of nanoparticles involves solvent evaporation and thickness reduction, which lead to stress formation in the film and the optical fiber. In addition, after sintering and on cooling, due to the difference between the Coefficients of Thermal Expansions (CTE) of silver and silica ($\alpha_{silver}=18.9 \times 10^{-6 \circ}$ C.$^{-1}$ and $\alpha_{silica}=0.55 \times 10^{-6 \circ}$ C.$^{-1}$), tensile/compressive stresses build up in the silver films/optical fiber. In FIG. 15, the wavelength spacing of the reflectivity peaks is approximately 400 pm which is consistent with the results obtained from (1) with $\Gamma=2$ mm. The Bragg wavelength shift to lower wavelengths is the result of compressive stress in the coated segments of the fiber. The graph obtained from the modeling is also plotted in the figure showing that the modeling results and the experimental results are in good agreement.

FIG. 16 shows the reflectivity of the upper sideband as a function of the Bragg wavelength in a thermal cycle ranging from 45° C. to 85° C. It was observed that the response of the reflectivity curve has a hysteresis behavior at temperatures lower than 45° C. This can be attributed to the existence of micro-porosity within the silver films. At temperatures higher than 45° C., the reflectivity reduces monotonically from 20% to 3% as temperature rises.

FIG. 17 depicts the Bragg wavelength shift as a linear function of temperature with a sensitivity of 17.3 pm/° C. In addition, the results obtained from modeling are plotted in FIG. 16 and FIG. 17, showing agreement between the modeling and the experimental results with a deviation of 5%. The variations of the reflectivity with temperature are the results of the changes in the amplitude of the strain components along the fiber. As mentioned before, the deposition and laser sintering of silver films cause the formation of residual stress in the coated segments of the optical fiber. This leads to a periodic distribution of strain, and as a result, the periodic variations of $n_{eff}$ and $\Lambda$ along the optical fiber. On heating, the state of stress in the silver films changes from tensile to compressive, whereas the reverse occurs in the optical fiber. In the uncoated segments of the optical fiber, the strain components are generated because of thermal expansions that are equal to $\alpha_{silica}\Delta T$. The strain components in the coated and uncoated segments of the FBG are schematically plotted in FIG. 18. As shown, the difference between the strain components reduces with temperature, which causes the reduction of the amplitude of $n_{eff}$ and $\Lambda$ and as a result the coefficient $\hat{K}$.

Figure 19:
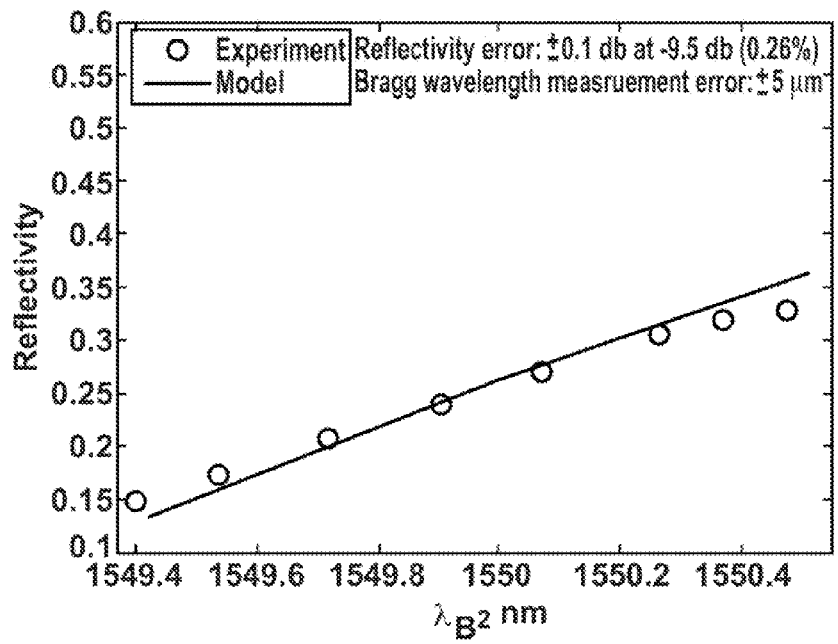
FIG. 19 shows a graph indicating reflectivity as a function of Bragg wavelength in tensile loading.

The structural parameter that is measured by FBGs is strain. To induce strain, an axial load is applied on the optical fiber. While there are various ways to apply axial loading, to apply the axial loading, the SFBG was installed on the test rig and tensile loads of 0-0.9 N were applied to the fiber. FIG. 19 shows the reflectivity of the first upper sideband as a function of the Bragg wavelength at a temperature of 45° C. during the tensile loading. According to this figure, the reflectivity increases to 32% by applying a tensile load of 0.9 N. Due to the existence of periodic films, tensile forces acting on the optical fiber produce the periodic strain distribution along the grating. The tensile force increases the amplitude of the strain distribution and that of $n_{eff}$ and $\Lambda$, which amplifies the sidebands reflectivity. The results, obtained from the opto-mechanical modeling in the figure are in agreement with the experimental data.

Figure 20:
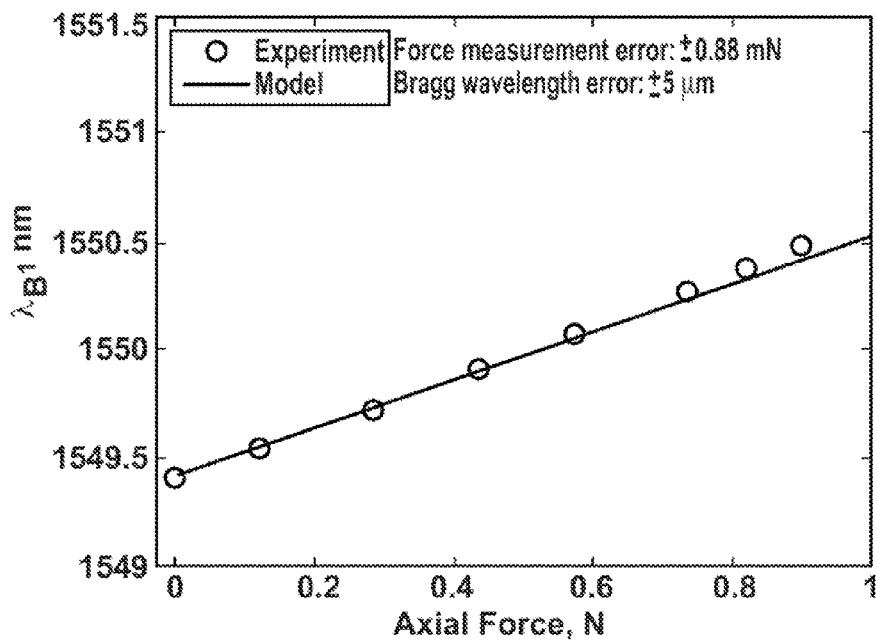
FIG. 20 shows a graph indicating Bragg wavelength as a function of tensile force.

FIG. 20 shows the corresponding Bragg wavelength shift as a function of the axial force. The shift of the Bragg wavelength has a sensitivity of 1.2 nm/N deviating from the modeling results by 9%. The linear behavior of the Bragg wavelength variations implies that the silver films are in elastic region, and there is no crack or delamination in the silver films.

It should be noted that the behavior of the modeling graphs is dependent on the initial residual stress formed in the coated segments of the optical fiber. In the analyses performed in this research, the model was tuned to fit the experimental data. The tuning was done by finding the initial residual stress for the best fit. In spite of this tuning, the model predicts the gradient and tendency of the results. Obtaining accurate values for the residual stress components requires microstructural analysis of the films.

Figure 21:
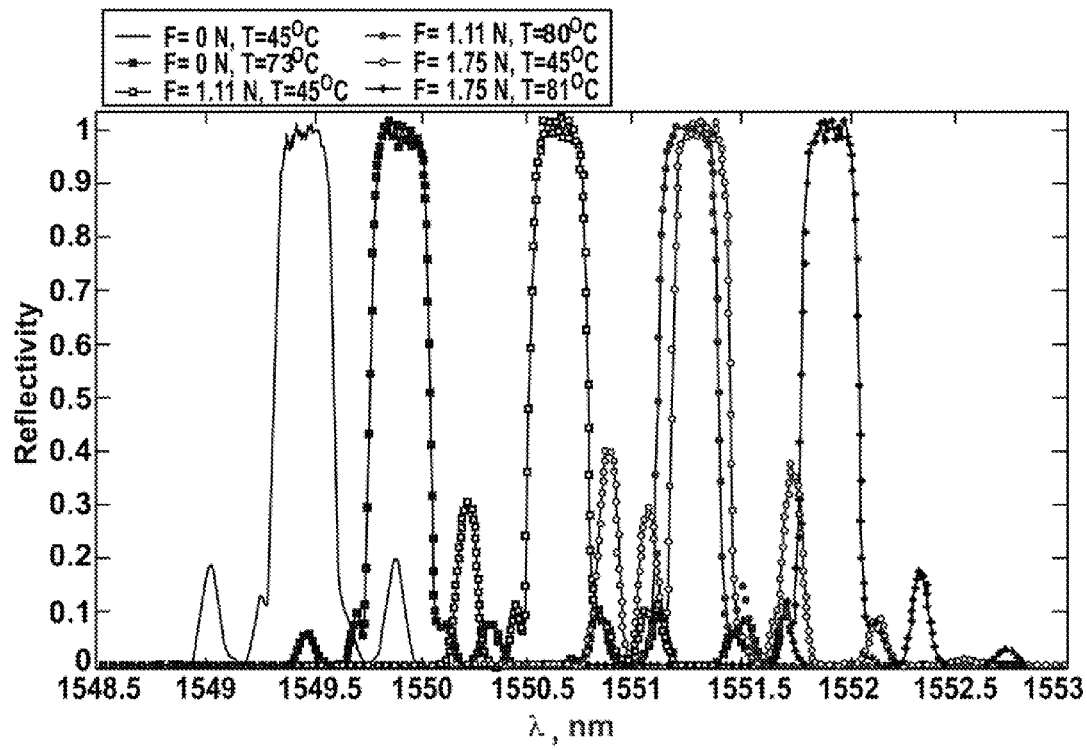
FIG. 21 shows a graph indicating reflectivity spectra of superstructure FBG under tensile force and temperature.
Figure 22:
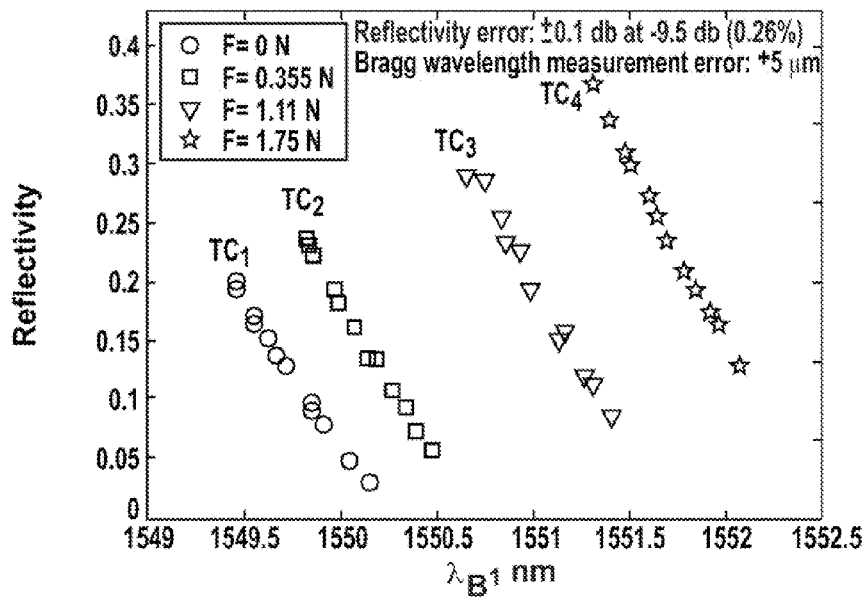
FIG. 22 shows a graph indicating reflectivity as a function of Bragg wavelength for the superstructure FBG under tensile force and temperature.

The capabilities of the developed SFBG sensor for the simultaneous measurement of strain and temperature were investigated. The experimental results are displayed in FIG. 21 to FIG. 23. FIG. 21 provides the spectra of SFBG at different temperatures and tensile forces. It is apparent from the figures that both structural loading and temperature shift the Bragg wavelength. As discussed above, structural load, inducing strain on the optical fiber, increases the reflectivity of the sidebands; however, temperature inversely affects the reflectivity. This feature enables the simultaneous measurement of strain and temperature using a single FBG. FIG. 22 contains the reflectivity vs. Bragg wavelength graphs for SFBG in multi-parameter sensing. The graphs are obtained by measuring the reflectivity and the Bragg wavelength in thermal cycles while the sensor is under tensile force.

When the sensor is exposed to tensile force and temperature variations, the strain can be directly obtained from FIG. 22 by locating the corresponding force graph from the Bragg wavelength and the reflectivity readings. The strain on the optical fiber is related to the applied force. Temperature is obtained by using the Bragg wavelength vs. temperature curves in FIG. 23.

For each sensor, a set of characteristic curves, similar to FIGS. 22 and 23, can be obtained to enable multi-parameter measurements. The characteristic curves are in the form of reflectivity vs. Bragg wavelength and Bragg wavelength vs. temperature. The characteristic curves are schematically plotted in FIG. 24. The plots consist of a series of constant-strain curves. Strain can be measured by using the reflectivity vs. Bragg wavelength graph (FIG. 24*a*). To obtain temperature, the corresponding constant strain curve is located in Bragg wavelength vs. temperature graph in FIG. 24*b*.

The experimental results show that the developed SFBG can simultaneously monitor temperature and strain in a temperature range of approximately 45° C. to 90° C. and an axial force range of approximately 0 N to 1.75 N. Compared with the state-of-the-art technology for the simultaneous measurement of strain and temperature and the compensation of the effect of temperature using FBGs, the developed SFBG sensor has some distinguishing characteristics. One of the features of the developed sensor is the measurement of two parameters using a single reflection spectrum of FBG. As a result, the new sensor does not increase the volume of the captured data, as opposed to the methods proposing the use of multiple sensors such as two FBGs or combined FBG-Fabry Perot cavity. The developed SFBG can also be utilized for the simultaneous measurement of strain and temperature as well as providing temperature compensation.

When it comes to packaging, the size of the sensor is not increased significantly from the original FBG; only a few micron thin-film coating is added to the optical fiber. This facilitates the miniaturization of the sensing packages. Consequently, there is no need for the development of new packaging technologies to accommodate this type of sensor. This is an improvement over methods that have been proposed using bi-materials when making the sensing device bulky.

As discussed, the thin-film fabrication process induces residual stress in the thin films and the optical fiber resulting in the formation of residual sidebands in the reflection spectrum. To have a systematic calibration procedure, the values of the residual stresses need to be known. The residual stresses can be predicted by using the sintering model of nanoparticles and also by the analysis of the crystal structure of the thin films. A characterization scheme can be developed to correlate the magnitude of the residual stress in the thin films to the geometrical features and the process parameters.

The modeling and design of SFBGs with periodically spaced on-fiber silver thin films described. The LAMM process was successfully utilized for the deposition of on-fiber silver thin films with a thickness of 9 μm. The developed SFBG was successfully tested for the simultaneous measurement of strain and temperature. To analyze the sensitivity of the developed sensor to strain, the SFBG sensor was loaded axially in a test rig. The temperature sensitivity was investigated by heating the optical fiber. The reflection spectrum of the SFBG has equally spaced sidebands whose intensities are tunable with temperature and strain. Concurrent reading of the sidebands reflectivities and the Bragg wavelength shift, the effects of temperature and strain can be separated in the reflection spectrum. A series of characteristic curves can be obtained for the calibration of the SFBG sensor. The characteristic curves consist of sideband reflectivity vs. Bragg wavelength and Bragg wavelength vs. temperature curves.

Two laser-based approaches were used for the development of the FBG-based sensors, including additive and subtractive methods, to increase FBGs' sensitivity and develop new sensors. In the additive method, thin films with specific patterns are fabricated on the outer surface of FBGs. In subtractive methods, sections of the FBG cladding layer are selectively removed. Laser direct microfabrication methods, including laser-assisted maskless microdeposition and femtosecond laser micromachining are used for additive and subtractive methods, respectively.

Various conventional deposition methods have been utilized for on-fiber thin-film fabrication. Another group of technologies that can be considered for the fabrication of on-fiber coatings is the Direct Write (DW) methods. In the DW methods, categorized as layered manufacturing technologies, the materials are selectively deposited in a layer-by-layer fashion at specific locations on substrates. Compared with conventional coating methods, the DW methods do not involve masks, and they are fast and inexpensive. Patterning with conventional thin-film deposition methods requires the addition and removal of materials which makes the use of masks inevitable.

The DW method that has been proposed and implemented in this research is Laser-Assisted Maskless Microdeposition (LAMM). In addition to the characteristics of the DW methods, LAMM has some distinguishing features enabling the deposition of thin films on optical fibers. The key feature of the LAMM process is conformal deposition on non-planar surfaces. Compared with other DW methods such as ink-jet printing in which the gap between the depositing head and the substrates is less than a few tens of microns, the gap in LAMM is around 1-5 mm. This enables the conformal and selective deposition on non-planar surfaces and three-dimensional substrates. In the following, the details of the LAMM process are explained.

In one embodiment, the LAMM processes was adopted for the deposition of on-fiber thin films. The LAMM equipment consists of four major components (FIG. 25):
1. Atomizers (ultrasonic and pneumatic),
2. Deposition unit (including processing head, nozzles, shutter, sheath gas, atomizer gas, and tubing),
3. Laser and optical head (including a CW Erbium fiber laser with the wavelength of 1550 nm),
4. Positioning stage.

Thin-film fabrication using the LAMM process is performed in two steps: (1) micro deposition, in which metal nanoparticles suspended in a liquid are atomized to aerosols, injected from the deposition head and impinge on a moving substrate and (2) laser post-processing, in which the laser beam is used for post-heating and sintering of the as-deposited material.

The complete setup of LAMM is illustrated in FIG. 25. The atomizers and positioning stage have been manufactured by OPTOMEC Inc. The deposited materials are in the form of nanoparticles suspended in liquid, called nano-ink. The nano-ink is placed in one of the atomizer systems.

The ultrasonic atomizer generates ultrasonic waves that are transferred to the nanoparticle solution. When the solution is exposed to the ultrasonic waves, minuscule droplets of the liquid are ejected at the gas-liquid interface and form a dense mist in the surrounding gas. This phenomenon is well described by cavitation and capillary wave hypotheses, for example as taught by Mir, J. M., "Cavitation-Induced Capillary Wave in Ultrasonic Atomization" Journal of Acoustical Society of America, vol. 67, pp. 201-205, 1980 and Rajan et. al., "Correlation to Predict Droplet Size in Ultrasonic Atomization" Journal of Ultrasonics, vol. 39, pp., 235-255, 2001, both of which are incorporated herein by reference.

In the pneumatic atomizer, a high velocity gas stream is used to shear a liquid stream into droplets. The liquid stream is generated through the Bernoulli effect which creates the flow of nanoparticle suspension from the reservoir. The atomizer systems have the capability to generate mist with droplet sizes of 1-5 microns. For the best performance, the values of viscosities of the liquid in the atomizers should be 0.7-10 cP for the ultrasonic atomizer and 1-2500 cP for the pneumatic atomizer.

The gas flow from the ultrasonic atomizer is directed to the deposition head. However the gas flow rate in the pneumatic atomizer is high for the deposition head. The aerosol generated in the pneumatic atomizer passes through Virtual Impactor module, where the excess gas is removed by a vacuum pump, and the aerosol and the remaining gas are carried to the deposition head.

The aerosol is carried to the deposition head by the flow of nitrogen gas. At the deposition head, the aerosol stream is mixed with a secondary gas stream of nitrogen, called sheath gas flow, and passes through a co-axial nozzle. This causes the aerodynamic focusing of the aerosol stream which then passes through a deposition tip with a diameter of 100 to 250 µm. The substrate is mounted on a two-degree-of-freedom moving stage, controlled by a motion control module. By moving the substrate relative to the deposition head, the desired patterns are produced in a layer-by-layer fashion. An electric heater, embedded in the stage, can heat the substrate up to 200° C.

For the deposition on optical fibers, an in-house rotational stage was designed and manufactured to equip LAMM with one additional degree of freedom. As illustrated in FIG. 26, the connectorized and stripped optical fiber is mounted at each end of the concentric rotational holders. The entire setup is mounted on the translational stage of the LAMM workstation.

For the laser post-processing, a CW single-mode erbium fiber laser with a wavelength of 1550 nm along with the associated optics was added to the LAMM workstation, as shown in FIG. 25. The focused laser beam has a diameter of 30 µm and delivers powers of 0.5 W to 3.5 W to the process zone. After the deposition, the laser beam irradiates the as-deposited materials and causes the agglomeration of the nanoparticles.

The laser sintering mechanism of nanoparticles is shown in FIG. 27. When the nanoparticles solution is radiated by the laser beam, the solvent evaporates and the particles agglomerate to form solid structures. As shown in FIG. 27, the agglomerated particles produce "neck-shape" structures. Agglomeration, which leads to the reduction of surface energy, occurs as a result of the atomic diffusion between the nanoparticles. Different diffusion mechanisms can occur in the laser sintering process: surface diffusion, grain boundary diffusion, and lattice diffusion. In the laser sintering of nanoparticles, the dominance of a diffusion mechanism depends on the size of nanoparticles. In the early stages of the sintering process, surface diffusion and grain boundary diffusion, with lower activation energies than lattice diffusion, are dominant.

Applying the laser energy to the process increases the density of the deposited films, resulting in an increased electrical conductivity. The laser sintering of nanoparticle solutions involve liquid evaporation and densification. As a result, weight loss and the formation of residual stress are prevalent in this process.

The parameters involved in the LAMM process fall into two groups of deposition and laser sintering, and are provided in Table 4.

TABLE 4

LAMM process parameters

| Deposition Process Parameters | Laser Sintering Process Parameters |
|---|---|
| Pneumatic Atomizer | Laser power (W) |
| Atomizer gas flow rate (cm³/min) | Laser scanning speed (mm/s) |
| Sheath gas flow rate (cm³/min) | Focused laser beam diameter (μm) |
| Virtual impactor gas flow rate (cm³/min) | |
| Deposition speed (mm/s) | |
| Deposition tip diameter (μm) | |
| Ultrasonic Atomizer | |
| Atomizer gas flow rate (cm³/min) | |
| Sheath gas flow rate (cm³/min) | |
| Atomizer voltage (V) | |
| Deposition speed (mm/s) | |
| Deposition tip diameter (μm) | |

As listed in Table 4, the LAMM process involves various parameters. To attain films with desired geometrical features and mechanical and microstructural properties, and investigate the effects of the process parameters on the final quality and characteristics of the deposited films, the process needs to be characterized. In the LAMM process, the deposition parameters primarily affect the geometrical features such as the thickness and width of the films. For the analysis of the microstructural and mechanical properties, the effects of the laser processing parameters should be investigated. The final goal is the deposition on the non-planar surface of optical fibers. However, in the current characterization scheme, the optimum parameters are obtained for planar substrates. Then, the parameters are further tuned for the deposition on the non-planar surface of optical fibers.

Silver nanoparticles suspended in ethylene glycol ($C_2H_4(OH)_2$) were used in the experiments. The suspension contained 50 wt. % of silver nanoparticles with an average particle size of 50 nm, supplied by Nano-Size Ltd.

The deposition, followed by laser sintering, was performed on planar silica ($SiO_2$) substrates at different process parameters. After the deposition and laser sintering, the samples were examined by optical microscope and scanning electron microscope (SEM) to study the microstructure of the deposited tracks. A BH2-UMA model Olympus microscope and a LEO 1530 Field Emission Scanning Electron Microscope (FE-SEM) were used for this purpose. In addition, white light interferometry using optical profilometery (WYKO NT 1100 optical profiling system, Veeco, Plainview, N.Y., USA) was utilized to study the geometrical features of the deposited films. The laser power at the process zone was measured by a power meter (L30A Thermal Head, OPHIR, Logan, Utah, USA). The crystalline structure of the thin films was examined with X-ray Diffraction (XRD) by using a micro X-ray diffraction machine with Cu—$K_\alpha$ radiation. To obtain the effect of laser parameters on the mechanical properties of the deposited thin films, nano-indentation tests were performed. For these tests, Hysitron TI 900 TriboIndenter (Hysitron, Inc., Minneapolis, Minn., USA) was utilized.

A Design of Experiments (DOE), based on the Taguchi method, was developed to optimize the process parameters and gain insight into the effects of the process parameters on the properties of the films. The optimization of the process parameters was based on the width and the thickness of the deposited films. The optimized process parameters for the deposition with pneumatic atomizer and ultrasonic atomizer are listed in Table 5 and Table 6. These process parameters result in fine-edge films with thicknesses of about 1 μm and widths of 20-50 μm.

TABLE 5

Deposition process parameters for pneumatic atomizer

| Parameter | Value |
|---|---|
| Atomizer flow rate (cm³/min) | 740-750 |
| Sheath gas flow rate (cm³/min) | 100-110 |
| Virtual impactor gas flow rate (cm³/min) | 700 |
| Deposition velocity (mm/s) | 3-5 |
| Deposition tip diameter (μm) | 200 |

TABLE 6

Deposition process parameters for ultrasonic atomizer

| Parameter | Value |
|---|---|
| Atomizer flow rate (cm³/min) | 7-12 |
| Sheath gas flow rate (cm³/min) | 40-55 |
| Atomizer voltage (V) | 35-40 |
| Deposition velocity (mm/s) | 0.5-10 |
| Deposition tip diameter (μm) | 150 |

Trials were conducted to deposit silver on planar fused silica substrates. FIG. 28 presents spiral and straight line patterns. The topography images of the samples taken by the optical profiling system are illustrated in FIG. 29.

Samples were fabricated with different laser powers at a laser speed of 0.25 mm/s. Laser powers of 1.35 W, 2.41 W, and 3.28 W at the process zone with a beam spot diameter of 200 μm were used in the experiments. FIGS. 30a and b and FIGS. 31a and b depict the microstructure of the samples taken by FE-SEM at magnifications of 20 kX and 35 kX. The figures show the changes in the microstructure during laser sintering. As seen, at the laser power of 1.35 W, the nanoparticles have been slightly sintered, and neck-shape formation is rarely seen in this sample. As the laser power increases, the agglomeration and neck-shape formation are observed in the nanoparticles. At the power of 3.28 W, which is the maximum achievable power in the LAMM system, close-packed sintered particles are observed.

In the characterization of the process, the crystal structure of silver films was also investigated. FIG. 32 shows the XRD spectra of unsintered films and the films sintered at laser powers of 2.41 W and 3.28 W. The existence of multiple peaks in the XRD spectra implies that the silver nanoparticles are polycrystalline. The magnified peaks at 44o associated with (200) planes are also shown in FIG. 33. According to the magnified image, the peak of the untreated sample is broader than that of laser-sintered samples. The Full-Width-at-Half-Maximum (FWHM) of the unsintered sample, and the samples sintered at 2.41 W and 3.28 W are is 0.77°, 0.65°, and 0.63°, respectively. The increase of the FWHM in the X-ray diffraction is related to the crystallite structure. As the laser power increases, the particles agglomerate and the level of periodic arrangement in the crystals increases. This results in sharper peaks when the X-ray beam is diffracted.

The mechanical properties including modulus of elasticity and hardness of the silver films were tested using nanoindentation tests. For the nanoindentation tests, an image of each sample was obtained by the nanoindenter tip, and six locations which were 10 μm apart were located. A maximum load of 1000 μN was applied at each location, and the load-displacement curves were obtained. FIG. 34 shows the indentation profiles of six locations in a sample taken by the nanoindenter tip.

FIG. 35 shows the load-displacement curves for each sample at five indentation locations, as shown in FIG. 34. According to the Oliver-Pharr method, as described in Oliver et all "An Improved Technique for Determining Hardness and Elastic Modulus using Load and Displacement Sensing Indentation Experiments" Journal of Materials Research, Vo. 7, no. 6, pp. 1564-1583, 1992, the indentation hardness (H) is obtained from $$H = \frac{P_m}{A} \quad (14)$$

where $P_m$ is the maximum applied load and A is the contact area between the indenter and the silver layer.

In addition, the nanoindentation test results were employed to obtain the modulus of elasticity of the deposited silver layers. The modulus of elasticity is related to the initial slope of the relaxation curve in the force-displacement graph as follows:

$$S = \frac{2\alpha^* E^* A^{1/2}}{\sqrt{\pi}} \quad (15)$$

where S is the initial slope of the relaxation curve, $\alpha^*$ is a correction factor for the shape of the indenter, and $E^*$ is the reduced modulus of elasticity which is related to the modulus of elasticity of the film and the indenter, as follows:

$$E^* = \left(\frac{1-v_f^2}{E_f} + \frac{1-v_{in}^2}{E_{in}}\right)^{-1} \quad (16)$$

where $v$ is the Poisson's ratio, and subscripts f and in denote the film and the indenter properties. The modulus of elasticity of the deposited silver films can be obtained by using (15) and (16) The mechanical properties of the indenter were $E_{in}=1140$ GPa and $v_{in}=0.07$ and $v_f=0.37$ was used for silver.

The hardness and modulus of elasticity, obtained from the nanoindentation test results, are plotted in FIG. 36 and FIG. 37. It is clear that hardness and modulus of elasticity increase by increasing the laser power. This is the result of the agglomeration and sintering of nanoparticles. Close values of hardness have been reported for silver thin films Cao et al. "Nanoindentation Measurements of the Mechanical Properties of Polycrystalline Au and Ag thin films on Silicon substrates: Effects of Grain Size and Film Thickness", Materials Science and Engineering: A, vol. 427, no. 1-2, pp. 232-240, 2006 and Panin et al., "Mechanical Properties of Thin Ag films on a Silicon Substrate Studied Using the Nanoindentation Technique", Physics of the Solid State, vol. 47, no. 11, pp. 2055-2059, 2005, the contents of each of which are incorporated herein by reference. In these experiments, the maximum obtained value for modulus of elasticity is 65 GPa, which is 21% less than that of bulk silver (83 GPa). This can be caused by the differences in the samples microstructure, affected by the type of the fabrication process. In addition, the agglomeration of the nanoparticles might not be complete and contain porosity. The surface morphology such as the roughness of the deposited silver layers can also cause the discrepancies.

Silver was selected as the coating material for FBGs. Among the precious materials that are available as nanoink, silver has a good adhesion with silica. In addition, the coefficient of thermal expansion of silver is high ($\alpha_{silver}=18.9\times10^{-6}$ C.$^{-1}$), compared with that of silica $\alpha_{silica}=0.55\times10^{-6}$ C.$^{-1}$ which increases the thermal sensitivity of the FBG sensor.

A FBG with a Bragg wavelength of 1550 nm and grating length of 14 mm (O/E LAND Inc., Quebec, QC, Canada) was selected. The optical fiber was coated with a polymeric layer to protect it during shipping and handling. The polymer coating was chemically stripped by immersing the fiber in acetone for 15 min.

During the deposition process, the FBG was mounted on the rotational stage in FIG. 26 and fixed at the ends to keep it straight under the deposition head. The films were deposited on the optical fiber by moving it in a programmed path relative to the deposition head. To coat a desired length of the fiber, silver tracks were deposited adjacent to each other with a distance of 20 to 25 μm. FIG. 38 shows the relative path followed by the deposition head.

During the deposition process, only one side of the optical fiber was exposed to the aerosol of silver nanoparticles. This causes non-uniformity in the thickness of the films around the fibers. To get a uniform coating thickness, the optical fiber was rotated by 90° in each round of depositions, as displayed in FIG. 39. The process parameters used for the deposition of on-fiber silver films are listed in Table 7.

FIG. 40 Shows the LAMM deposition head during the deposition of the periodic patterns of silver coating on an optical fiber.

FIG. 41 display the periodic silver coatings deposited on an optical fiber to create a superstructure FBG. Films were deposited with a period of 2 mm, duty cycle of ¾, and thickness of 9 μm. Totally, seven coating segments with a length of 1.5 mm were fabricated. The optical fiber has a diameter of 125 μm, and the average diameter of the coatings is 143 μm. FIG. 42 illustrates the measured values of the film thickness at different angles around the fiber. As observed, the film is uniformly distributed around the optical fiber.

TABLE 7

LAMM process parameters for the deposition of silver films on optical fibers

| Parameter | Value |
| --- | --- |
| Aerosol flow rate (cm³/min) | 45-50 |
| Deposition velocity (mm/s) | 3 |
| Laser power at the process zone (W) | 3.3 |
| Laser scanning speed (mm/s) | 0.25 |
| Laser spot size at the core of optical fiber (μm) | 200 |
| Deposition tip inside diameter (μm) | 200 |

In another embodiment, an optic fiber capable of simultaneous measurement of more than one criteria is created by the selective inscription of micro-grooves on the outer surface of the FBG optical fiber. This makes FBGs sensitive to the index of refraction and the concentration of the surrounding medium. Laser direct micromachining is one method chosen for the inscription of micro-grooves; however other methods of inscribing the surface of the fiber optic may also be used. In this method, Ultrashort laser pulses in the range of femtosecond ($10^{-15}$ s) enable the fabrication of features with submicron precision in a large group of materials, specifically transparent dielectrics such as silica. Due to the non-linear phenomena occurring in the interactions of ultrashort pulse lasers with dielectric materials, these lasers can effectively be used for micromachining and structural modifications of transparent materials, such as silica. In this regard, micromachining of optical fiber sensors can be performed with femtosecond lasers. A femtosecond pulse laser is utilized to micromachine FBGs to enhance their performance for multi-parameter sensing.

The diameter of FBGs can also be reduced by etching with hydrofluoric acid ("HF etching"). However, the HF etching rate is slow and the process is isotropic and non-directional. Etching rates of 1.8 µm/min with 52% HF solution, 80 nm/min in buffered oxide etch (BOE), and 650 nm/min in 24% buffered HF solution are typical for the reduction of the cladding diameter of FBGs.

Compared with HF etching, the femtosecond laser micromachining process is faster and can be easily controlled for patterning on optical fibers. The optical fiber, made of silica, is transparent to the visible and Near-Infrared (NIR) electromagnetic radiation. Long pulse lasers (pulse durations of 10 ps and larger) cannot be absorbed by silica for micromachining. However, ultrashort laser pulses (tenth of picoseconds or femtosecond) in the NIR range enable both surface and bulk micromachining of silica.

The interaction of ultra-short laser pulses with materials differs completely from that of long pulse lasers. In the interaction of long pulse lasers (pulse durations larger than 10 ps) with materials, the laser energy absorption mechanism is electronic excitation due to the absorption of electromagnetic radiation and the electron-lattice interaction to convert the energy to heat.

The interaction of femtosecond laser pulses with dielectrics such as silica involves some fundamental processes. When silica is irradiated by intense femtosecond laser pulses, the index of refraction of the material becomes intensity dependent. The energy of a single photon is not sufficient to excite the electrons in the valence band and transfer them to the conduction band. As a result, in the interaction of high density laser pulses, the electrons in the valence band are excited through the absorption of multiple photons which is called multi-photon ionization. The rate of the multi-photon ionization is a function of the laser intensity. The electrons in the conduction band can absorb more laser energy through free-carrier absorption. If the energy of the conduction electrons increases by an amount higher than that of the band gap, the conduction electrons can ionize more valence electrons through impact ionization. This process continues as long as the laser energy is available, and results in increase of the plasma density, which is known as avalanche ionization. After the formation of the plasma, various mechanisms can cause damage in the dielectric material. The transfer of energy from the high density plasma results in melting, vaporization, and ablation of the material. The transfer of energy from the high density plasma to the lattice occurs in a time scale much smaller than the thermal diffusion time, which reduces the heat affected zone. The damage can also result from the defects originated from the creation and relaxation of Self-Trapped Excitons (STE). The generated defects in silica are oxygen vacancy (E' center), peroxy radical/linkage, and Non-Bridging Oxygen Hole Center (NBOHC).

In addition to surface micromachining and material removal, structural modifications, including changes in the index of refraction and stress induction, can be achieved in the interaction of femtosecond laser pulses with silica. Femtosecond lasers have been used for the induction of birefringence in optical fibers by exposing the cladding to the laser radiation and for direct writing of Bragg gratings in the core of optical fibers for sensing and fiber laser applications. The fabrication of intracore Bragg gratings by the lateral illumination of optical fibers using phase mask scanning technique has been reported to enhance the sensing performance of FBGs. Femtosecond lasers have been used for the inscription of high-temperature stable Bragg gratings in Polarization Maintaining (PM) optical fibers. The photo-enhanced birefringence, caused by the femtosecond pulses, resulted in FBG sensors with a dual-parameter sensing capability in a wide range. Bragg gratings have also been inscribed in the core of the Yb-doped optical fibers used in fiber lasers.

FIG. 43 shows a workstation setup which can be used for femtosecond laser etching. FIG. 44 is a schematic diagram of a femtosecond laser setup, and the position of the optical fiber relative to the laser beam. The Libra-S laser system, a diode-pumped Ti:Sapphire femtosecond laser (Coherent Inc., Santa Clara, Calif., USA) can be used for the femtosecond etching. The laser produces light of 800 nm wavelength in 100 fs pulses with a repetition rate of 1 kHz. In one embodiment, the laser beam was defocused on the fiber cladding surface to create larger features. The circular shape of the optical fiber gives a non-circular intensity distribution at the process zone. In this case, the beam diameter along the optical fiber axis (z axis) is smaller than that in the direction perpendicular to the optical fiber axis (x axis).

In another embodiment, micro-grooves can be etched at various laser average powers. FIG. 45 illustrates the variations of the grooves' width as functions of the laser power and a laser scanning speed of 5 µm/s. The width of micro-groves increases by increasing laser power. A micro-groove width of less than 20 µm is achievable at laser powers of less than 50 mW. Further, the roughness of the micro-groove edges increases by increasing the laser scanning speed. This can be attributed to the number of pulses per spot.

For the inscription of micro-grooves on optical fibers, the fibers can be mounted on the three-dimensional moving stage and irradiated by the laser beam. The stage can be programmed to move the optical fiber across the laser beam to inscribe micro-grooves.

FIG. 46 shows micro-grooves inscribed on the surface of an optical fiber at a laser average power of 41 mW and laser scanning speeds of 100 µm/s and 500 µm/s. For these two cases the numbers of pulses per spot are 175 and 33 on the center line, respectively. At lower scanning speeds, smoother groove edges were formed due to the increased number of pulses per spot and less temporal separation between the pulses.

FIG. 47 shows the removal of material with a specific pattern from the outer surface of FBGs. The design parameters are the geometries of the patterns including b, w, $w_1$, $w_2$, $w_i$, $r_d$, $r_{d1}$, and $r_{d2}$. $r_f$ is the original diameter of the optical fiber. Similar to the additive method, in the cutting method the depth of grooves can vary up to 40 µm, the width and spacing each can be up to one-third of the length of the grating.

The optical fiber described in the present disclosure also has application in the diagnosis of disease such as cancer. The success of cancer treatment is highly dependent on the acquisition of accurate data on tumor microenvironmental factors such as the interstitial fluid pressure, hypoxia, and acidosis, which directly affect the drug action/delivery and metastasis.

The optical fiber sensors described in this application can be used for the simultaneous measurement of these factors in tumor tissues.

Currently used sensors have significant limitations, such as sensitivity to electromagnetic disturbances and the risk of depositing residual materials in deep tissues. In addition, there are severe limitations to their use for the concurrent measurement of the three relevant parameters in cancerous tissues.

The conventional methods of interstitial fluid pressure measurement are wick catheter, wick-in-needle technique, glass micropipette/servonul I transducer, semiconductor tipped Millar transducer, and subcutaneous capsule implantation. The most common method of monitoring the level of oxygen in tumors is the polarographic needle electrode developed by Eppendorf. In addition, pH can be indirectly measured by Magnetic Resonance Spectroscopy (MRS). The conventional sensors for IFP and tumor hypoxia are basically designed for the detection of a single parameter. In addition, the presence of metal parts prevents their applications in Magnetic Resonance (MR) scanners. Furthermore, their usage is limited due to the risk of leaving residual materials in deep tissues. In addition, in case of concurrent measurement of multi-parameters, masses of wires and several devices are required to collect data.

Optical fiber biosensors have the potential to overcome the limitations of current technology used in cancer therapy to measure the aforementioned parameters. Compared with their electromagnetic counterparts, optical fiber sensors are advantageous; they are small (approximately 125 μm in diameter), electrically insulated as they are made of silica, robust to electromagnetic disturbances, and corrosion-resistant to most biological agents. Probes utilizing optical fiber sensors such as those presently disclosed with multi-parameter sensing capability can be used for such measurements in tumors. The use of an individual strand of optical fiber requires only a single spectrum of light to be captured and analyzed to obtain the values of parameters.

The transduction mechanisms that can be used for parameters detection are essentially the changes in index of refraction and mode coupling in optical fiber gratings. The fabrication of the biosensors involves a series of processes such as selective and layer-by-layer deposition of thin films on optical fibers and selective laser micromachining of optical fibers. Conventional microfabrication methods such as lithography may not be efficient for these purposes, as they increase the complexity and production cost due to addition and removal of materials. In this regard, novel laser direct microfabrication methods can be utilized. The unique characteristics of the laser beam, i.e. coherence and monochromaticity, provide the potential for the direct fabrication of optical fiber biosensors in the micro-scale. In addition, since laser microfabrication is a non-contact process, it does not leave external residues on the sensors which are intended to be used for in-vitro and in-vivo studies. Laser micromachining using ultrafast pulsed lasers, e.g. femtosecond, can be employed to selectively micromachine and make special patterns on the outer surface of the optical fibers. In addition, laser-assisted microdeposition techniques can be utilized to selectively deposit thin films.

In the preceding description, for purposes of explanation, numerous details are set forth in order to provide a thorough understanding of the embodiments. However, it will be apparent to one skilled in the art that these specific details are not required.

The above-described embodiments are intended to be examples only. Alterations, modifications and variations can be effected to the particular embodiments by those of skill in the art without departing from the scope, which is defined solely by the claims appended hereto.

What is claimed is:

1. An optical fiber sensor comprising a single Fiber Bragg Grating (FBG) provided to an optical fiber and a plurality of bands formed on a surface of the optical fiber in a spaced relationship to the single FBG wherein the optical fiber sensor provides simultaneous detection of more than one criteria.

2. The optical fiber sensor of claim 1, wherein the sensor simultaneously detects two criteria, the two criteria selected from the group consisting of temperature and strain, temperature and stress, temperature and pressure, temperature and force, temperature and level of hydrogen, and temperature and humidity.

3. The optical fiber sensor of claim 1, wherein the plurality of bands formed on the surface of the optical fiber comprise a plurality of coatings formed on an exterior of the optical fiber.

4. The optical fiber sensor of claim 3, wherein the plurality of coatings are equally spaced along a length of the FBG.

5. The optical fiber sensor of claim 4, wherein the plurality of coatings have a length of approximately 1.5 mm and a space between adjacent coatings of approximately 0.5 mm.

6. The optical fiber sensor of claim 3, wherein the plurality of coatings are non-equally spaced along a length of the FBG.

7. The optical fiber sensor of claim 3, wherein the plurality of coatings comprises a first set of coatings and a second set of coatings, the first set of coatings being equally spaced along a length of the FBG, and the second set of coatings being non-equally spaced along the length of the FBG.

8. The optical fiber sensor of claim 3, wherein the plurality of coatings are a film having a thickness of up to about 200 μm.

9. The optical fiber sensor of claim 8, wherein the plurality of coatings are a film having a thickness of about 9 μm.

10. The optical fiber sensor of claim 3, wherein the plurality of coatings have a length of up to one-third of a length of the FBG, and a space between adjacent coatings is up to one-third of the length of the FBG.

11. The optical fiber sensor of claim 1, wherein the plurality of bands are formed by removing a portion of a coating on the optical fiber.

12. The optical fiber sensor of claim 11, wherein the bands have a depth of up to 40 μm from the surface of the optical fiber to a bottom of the bands.

13. The optical fiber sensor of claim 12, wherein each of the plurality of bands have a length of up to one-third of a length of the FBG, and a space between adjacent bands is up to one-third of the length of the FBG.

14. The optical fiber sensor of claim 11, wherein the more than one criteria are selected from the group consisting of temperature and strain, temperature and force, temperature and stress, temperature and pressure, and temperature and liquid concentration.

15. A method of making an optical fiber sensor for simultaneously detecting more than one criteria, the method comprising:
    forming a single Fiber Bragg Grating (FBG) on a surface of the optical fiber; and
    forming a plurality of bands onto the optical fiber in a spaced relationship to the single FBG.

16. The method of claim 15, wherein the plurality of bands are applied by a procedure selected from the group consisting of direct writing, direct deposition, direct printing, layer-by-layer deposition, direct additive manufacturing, solid free-form fabrication, and layered manufacturing.

17. The method of claim 15, wherein the more than one criteria are selected from the group consisting of temperature and strain, temperature and stress, temperature and pressure, temperature and level of hydrogen, and temperature and humidity.

18. The method of making an optical fiber sensor of claim 15, wherein the plurality of bands is formed by removing coating material from a surface of the optical fiber.

19. The method of claim 18, wherein the coating material is removed by femtosecond laser etching of the surface of the optical fiber.

20. The method of claim 18, wherein the coating material is removed by selectively applying Hydrofluoric acid to the surface of the optical fiber.

21. The method of claim 18, wherein the more than one criteria are selected from the group consisting of temperature and strain, temperature and force, temperature and stress, temperature and pressure, and temperature and liquid concentration.

22. The method of claim 18, wherein the coating material is removed from a circumference of the optical fiber to form a plurality of circumferential bands along the optical fiber, the bands being formed having a depth of up to 40 μm from the surface of the optical fiber.

23. The method of claim 22, wherein the bands have a length of up to one third of a length of the FBG, and each band is spaced from an adjacent one of said bands at a distance of up to one third of the length of the FBG.

24. The method of claim 15, wherein the plurality of bands comprise a coating applied on an exterior of the optical fiber.

* * * * *